United States Patent
Aisaka et al.

(10) Patent No.: US 12,183,449 B2
(45) Date of Patent: Dec. 31, 2024

(54) DIAGNOSIS SUPPORT PROGRAM, DIAGNOSIS SUPPORT SYSTEM, AND DIAGNOSIS SUPPORT METHOD

(71) Applicant: Sony Group Corporation, Tokyo (JP)

(72) Inventors: Kazuki Aisaka, Kanagawa (JP); Takeshi Kunihiro, Kanagawa (JP); Kenji Yamane, Kanagawa (JP); Shinji Watanabe, Tokyo (JP)

(73) Assignee: Sony Corporation, Tokyo (JP)

( * ) Notice: Subject to any disclaimer, the term of this patent is extended or adjusted under 35 U.S.C. 154(b) by 363 days.

(21) Appl. No.: 17/433,566

(22) PCT Filed: Dec. 25, 2019

(86) PCT No.: PCT/JP2019/050880
§ 371 (c)(1),
(2) Date: Aug. 24, 2021

(87) PCT Pub. No.: WO2020/174863
PCT Pub. Date: Sep. 3, 2020

(65) Prior Publication Data
US 2022/0148714 A1    May 12, 2022

(30) Foreign Application Priority Data
Feb. 28, 2019    (JP) .................. 2019-036899

(51) Int. Cl.
*G16H 30/40* (2018.01)
*G02B 21/36* (2006.01)
*G06T 7/00* (2017.01)
*G06T 7/11* (2017.01)
*G16H 50/20* (2018.01)

(52) U.S. Cl.
CPC .......... *G16H 30/40* (2018.01); *G02B 21/368* (2013.01); *G06T 7/0012* (2013.01); *G06T 7/11* (2017.01);
(Continued)

(58) Field of Classification Search
CPC ........ G16H 30/40; G16H 50/20; G16H 50/30; G02B 21/368; G06T 7/0012; G06T 7/11;
(Continued)

(56) References Cited

U.S. PATENT DOCUMENTS

2012/0188283 A1    7/2012   Ohashi
2013/0188857 A1*   7/2013   Yoshihara .......... G01N 33/5091
                                                       382/133
(Continued)

FOREIGN PATENT DOCUMENTS

EP         1879116 A2      1/2008
JP      2012-155455 A      8/2012
(Continued)

OTHER PUBLICATIONS

Miori Maruya et al: "A Study on Importance Estimation of Medical Images by Learning User's Operation History", ITE Technical Report, Eizo Joho Media Gakkai, Tokyo, JP, vol. 35, No. 9, Feb. 14, 2011 (Feb. 14, 2011), pp. 41-45, XP009529893, ISSN: 1342-6893, DOI: 10.11485/ITETR.35.9.0_ 41 [retrieved on Sep. 21, 2017].
(Continued)

*Primary Examiner* — Qian Yang
(74) *Attorney, Agent, or Firm* — Wolf, Greenfield & Sacks, P.C.

(57) ABSTRACT

A diagnosis support program causes a computer to execute a derivation procedure of deriving, on the basis of a first pathological image corresponding to a first affected tissue, history information regarding a history of viewing the first pathological image, and diagnostic information for the first affected tissue corresponding to the first pathological image, diagnosis support information for supporting diagnosis of a second pathological image corresponding to a second affected tissue to be diagnosed.

21 Claims, 22 Drawing Sheets

(52) U.S. Cl.
CPC ... *G16H 50/20* (2018.01); *G06T 2207/10056* (2013.01); *G06T 2207/20081* (2013.01); *G06T 2207/30024* (2013.01); *G06T 2207/30096* (2013.01)

(58) Field of Classification Search
CPC . G06T 2207/10056; G06T 2207/20081; G06T 2207/30024; G06T 2207/30096
See application file for complete search history.

(56) References Cited

U.S. PATENT DOCUMENTS

| | | | | |
|---|---|---|---|---|
| 2014/0036058 | A1* | 2/2014 | Takahashi | H04N 7/18 348/80 |
| 2020/0380675 | A1* | 12/2020 | Golden | G06T 7/143 |

FOREIGN PATENT DOCUMENTS

| | | |
|---|---|---|
| JP | 2015-116319 A | 6/2015 |
| JP | 6400304 B2 | 10/2018 |

OTHER PUBLICATIONS

Written Opinion and English translation thereof mailed Mar. 31, 2020 in connection with International Application No. PCT/JP2019/050880.
International Preliminary Report on Patentability and English translation thereof mailed Sep. 10, 2021 in connection with International Application No. PCT/JP2019/050880.
Extended European Search Report issued Mar. 23, 2022 in connection with European Application No. 19916878.2.
International Search Report and English translation thereof mailed Mar. 31, 2020 in connection with International Application No. PCT/JP2019/050880.
Beaumann et al., Annotation of Whole Slide Images Using Touchscreen Technology. Roche. 2015. 1 page.
Maruya et al., A Study on Importance Estimation of Medical Images by Learning User's Operation History. ITE Technical Report. The Institute of Electronics, Information and Communication Engineers. Feb. 2011;35(9):41-45.

* cited by examiner

| SAMPLING | CENTER COORDINATES | MAGNIFICATION | TIME |
|---|---|---|---|
| 1 | (X1, Y1) | 1.25 | 0:00:00 |
| 2 | (X2, Y2) | 1.25 | 0:00:30 |
| 3 | (X2, Y2) | 20 | 0:01:00 |
| 4 | (X2, Y2) | 20 | 0:01:30 |
| 5 | (X3, Y3) | 20 | 0:02:00 |
| 6 | (X3, Y3) | 40 | 0:02:30 |
| 7 | (X3, Y3) | 40 | 0:03:00 |
| 8 | (X3, Y3) | 40 | 0:03:30 |
| ... | ... | ... | ... |

| PATIENT ID | PATHOLOGICAL IMAGE | DIAGNOSIS RESULT | GRADE | TISSUE TYPE | GENETIC TESTING | ULTRASONOGRAPHY | MEDICATION |
|---|---|---|---|---|---|---|---|
| XXX1 | Img1 | BREAST CANCER | 1 | NON-INVASIVE DUCTAL CARCINOMA | ER- | XXX | |
| XXX2 | Img2 | NORMAL | - | - | - | - | - |
| XXX3 | Img3 | BREAST CANCER | 3 | INVASIVE DUCTAL CARCINOMA | ER+ | YYY | XXX DOSED |
| XXX4 | ... | ... | ... | ... | ... | ... | ... |

| PATIENT ID | PATHOLOGICAL IMAGE | DIAGNOSIS RESULT | GRADE | TISSUE TYPE | GENETIC TESTING | CT EXAMINATION | MEDICATION |
|---|---|---|---|---|---|---|---|
| XXX1 | Img1 | LUNG CANCER | T1cN1 | SQUAMOUS CELL CARCINOMA | EGFR MUTATION | XXX | |
| XXX2 | Img2 | NORMAL | - | - | - | - | - |
| XXX3 | Img3 | LUNG CANCER | T3M1a | SMALL CELL CANCER | ALK FUSION GENE | YYY | XXX DOSED |
| XXX4 | ... | ... | ... | ... | ... | ... | ... |

| PATIENT ID | PATHOLOGICAL IMAGE | DIAGNOSIS RESULT | GRADE | TISSUE TYPE | GENETIC TESTING | ENDOSCOPIC EXAMINATION | MEDICATION |
|---|---|---|---|---|---|---|---|
| XXX1 | Img1 | ULCERATIVE COLITIS | 1 | - | - | XXX | |
| XXX2 | Img2 | NORMAL | - | - | - | - | - |
| XXX3 | Img3 | ULCERATIVE COLITIS | 2 | - | - | YYY | XXX DOSED |
| XXX4 | ... | ... | ... | ... | ... | ... | ... |

DIAGNOSIS SUPPORT PROGRAM, DIAGNOSIS SUPPORT SYSTEM, AND DIAGNOSIS SUPPORT METHOD

CROSS-REFERENCE TO RELATED APPLICATIONS

This application claims the benefit under 35 U.S.C. § 371 as a U.S. National Stage Entry of International Application No. PCT/JP2019/050880, filed in the Japanese Patent Office as a Receiving Office on Dec. 25, 2019, which claims priority to Japanese Patent Application Number JP2019-036899, filed in the Japanese Patent Office on Feb. 28, 2019, each of which is hereby incorporated by reference in its entirety.

TECHNICAL FIELD

The present disclosure relates to a diagnosis support program, a diagnosis support system, and a diagnosis support method.

BACKGROUND ART

In recent years, there has been developed a technology of adding a mark (hereinafter referred to as an annotation) to a medical image, which is a pathological image or the like, as a region to which attention is to be paid, such as a region where a lesion area may exist. For example, Non-Patent Document 1 described below discloses a technology of displaying an attention region by learning hematoxylin and eosin (HE. common histological stain) image data to which an annotation is added. According to this technology, it is also considered that an accuracy of diagnosis can be improved.

CITATION LIST

Non-Patent Document

Non-Patent Document 1: "Annotation of Whole Slide Images Using Touchscreen Technology"; Jessical L. Baumann, Kari Garsha, Mike S. Flores, Faith Ough, Ehab A. ElGabry; Roche

SUMMARY OF THE INVENTION

Problems to be Solved by the Invention

However, in the conventional technology described above, enormous man-hours are required to improve the diagnosis accuracy. Specifically, the work of adding an annotation to a pathological image is performed manually, for example, and thus requires a lot of time and workers. That is, it is difficult to easily improve the diagnosis accuracy in the conventional technology described above.

Thus, the present disclosure has been made in view of the above, and proposes a diagnosis support program, a diagnosis support system, and a diagnosis support method capable of improving diagnosis accuracy.

Solutions to Problems

In order to solve the above problem, a diagnosis support program according to one mode of the present disclosure causes a computer to execute a derivation procedure of deriving, on the basis of a first pathological image corresponding to a first affected tissue, history information regarding a history of viewing the first pathological image, and diagnostic information for the first affected tissue corresponding to the first pathological image, diagnosis support information for supporting diagnosis of a second pathological image corresponding to a second affected tissue to be diagnosed.

BRIEF DESCRIPTION OF DRAWINGS

FIG. 8 is a diagram illustrating an example of a viewing history storage unit included in a server.

FIG. 9A is a diagram illustrating a diagnostic information storage unit included in a medical information system.

FIG. 9B is a diagram illustrating a diagnostic information storage unit included in the medical information system.

FIG. 9C is a diagram illustrating a diagnostic information storage unit included in the medical information system.

MODE FOR CARRYING OUT THE INVENTION

Figure 1:
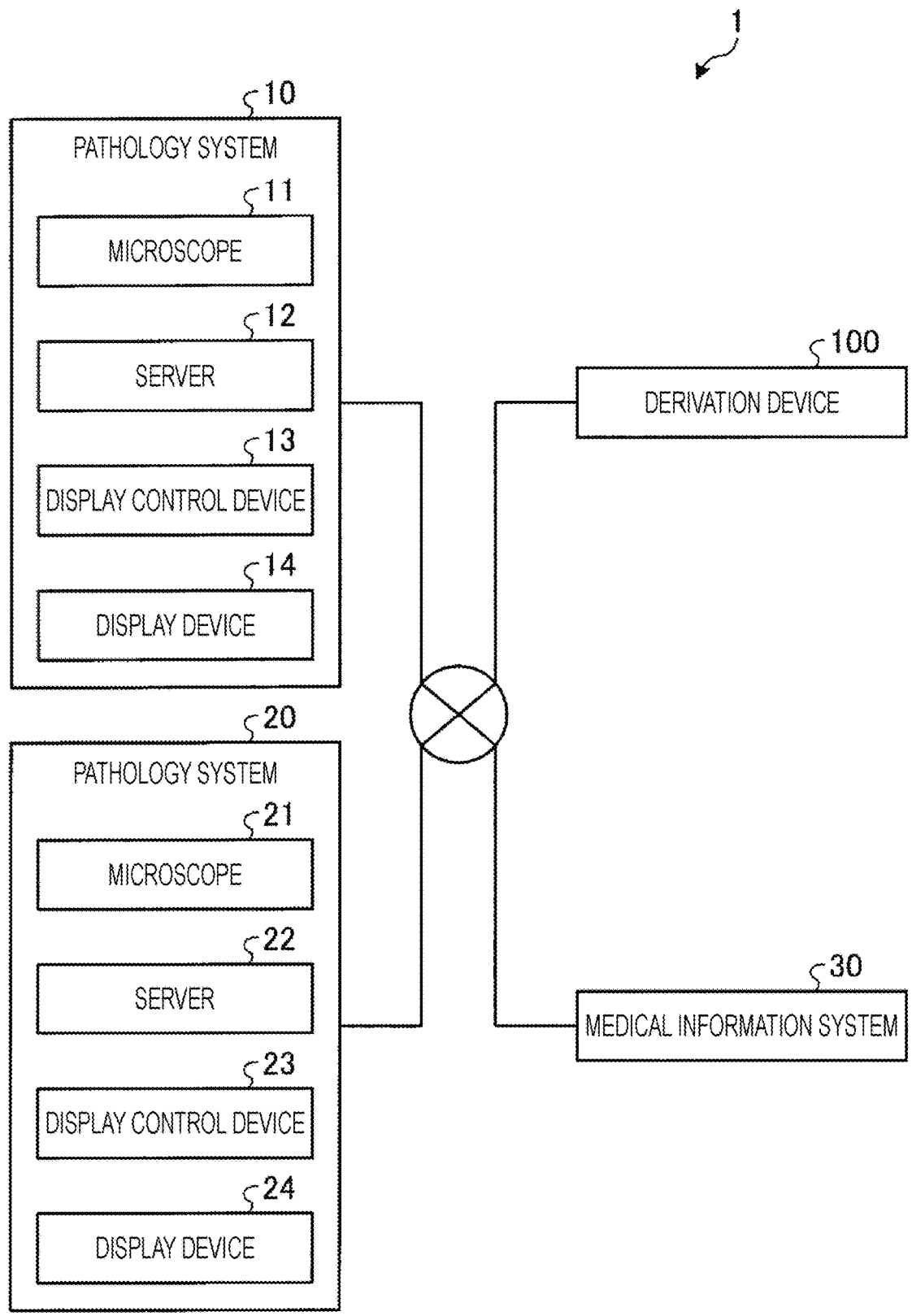
FIG. 1 is a diagram illustrating a diagnosis support system 1 according to a first embodiment.

Hereinafter, embodiments of the present disclosure will be described in detail with reference to the drawings. Note that, in each of the following embodiments, the same portions are denoted by the same reference numerals, and duplicate description will be omitted.

The present disclosure will be described in the order of items described below.
<First embodiment>
1. Configuration of system according to first embodiment
2. Various types of information
2-1. Pathological image
2-2. Viewing history information
2-3. Diagnostic information
3. Device configuration
3-1. Derivation device according to first embodiment
3-2. Display control device according to first embodiment
4. Processing procedure
4-1. Learning processing procedure according to first embodiment
4-2. Derivation processing procedure according to first embodiment
5. Modified examples 1
5-1. Display example (1) to 5-10. Display example (10)
5-11. Pathological images with different imaging conditions
5-12. Diagnosis prediction result
6. Modified examples 2
6-1. Learning processing (1) to 6-8. Learning processing (8)
<Second embodiment>
<Other embodiments>

FIRST EMBODIMENT

1. Configuration of System According to First Embodiment

First, a diagnosis support system 1 according to a first embodiment will be described with reference to FIG. 1. FIG. 1 is a diagram illustrating the diagnosis support system 1 according to the first embodiment. As illustrated in FIG. 1, the diagnosis support system 1 includes a pathology system 10, a pathology system 20, a medical information system 30, and a derivation device 100.

The pathology system 10 is mainly used by a pathologist, and is used in, for example, a laboratory or a hospital. As illustrated in FIG. 1, the pathology system 10 includes a microscope 11, a server 12, a display control device 13, and a display device 14.

The microscope 11 is an imaging device that has a function of an optical microscope, images an observation target contained in a glass slide, and acquires a pathological image (an example of a medical image), which is a digital image. Note that the observation target is, for example, a tissue or a cell collected from a patient, such as a piece of meat of an organ, saliva, or blood.

The server 12 is a device that stores and saves a pathological image captured by the microscope 11 on a storage unit (not illustrated). In a case where a viewing request has been received from the display control device 13, the server 12 retrieves a pathological image from a storage unit (not illustrated) and sends the retrieved pathological image to the display control device 13.

The display control device 13 sends, to the server 12, a pathological image viewing request received from a user. Then, the display control device 13 controls the display device 14 to display the pathological image received from the server 12.

The display device 14 has a screen using, for example, liquid crystal, electro-luminescence (EL), or cathode ray tube (CRT). The display device 14 may support 4K or 8K, or may be constituted by a plurality of display devices. The display device 14 displays the pathological image controlled to be displayed by the display control device 13. Note that, as described latter in detail, the server 12 stores viewing history information regarding a region of the pathological image observed by a pathologist via the display device 14.

The pathology system 20 is used in a hospital different from a hospital in which the pathology system 10 is used. The pathology system 20 includes a microscope 21, a server 22, a display control device 23, and a display device 24. Each unit included in the pathological diagnosis system 20 is similar to that of the pathology system 10, and thus description thereof will be omitted.

The medical information system 30 stores information regarding diagnosis of a patient. For example, in a case where it is difficult to diagnose a disease state only from an image in an endoscopic examination or the like in a predetermined hospital, a biopsy may be performed for a definite diagnosis based on a pathological diagnosis. A tissue specimen prepared from tissue collected from a patient is imaged by the microscope 11 of the pathology system 10, and a pathological image obtained by the imaging is saved to the server 12. The display control device 13 causes the display device 14 to display the pathological image, and a pathologist using the pathology system 10 makes a pathological diagnosis. The doctor makes a definite diagnosis on the basis of the pathological diagnosis result, and the definite diagnosis result is stored in the medical information system 30. The medical information system 30 stores information for identifying a patient, information about a patient's disease, examination information and image information used for diagnosis, a diagnosis result, and information regarding diagnosis such as prescription medication. Note that the medical information system 30 is referred to as an electronic medical record system or the like.

Incidentally, the accuracy of pathological diagnosis varies depending on the pathologist. Specifically, a diagnosis result based on a pathological image may vary from pathologist to pathologist, depending on years of experience, expertise, and the like of the pathologist. Given such a situation, in recent years, a technology for deriving diagnosis support information, which is information for supporting diagnosis by using machine learning, has been developed for the purpose of supporting pathological diagnosis. Specifically, a technology for estimating a region to which attention is to be paid in a new pathological image by preparing a plurality of pathological images in which a region to which attention is to be paid in the pathological image is annotated and analyzing the plurality of pathological images has been proposed. This allows for providing a pathologist with a region to which attention is to be paid in a pathological image, and thus diagnosis by the pathologist is supported.

However, when a pathologist makes a pathological diagnosis, the pathologist only observes a pathological image, and rarely adds an annotation to a region that influences a diagnosis of a lesion area or the like. Thus, in the technology of deriving diagnosis support information by using machine learning described above, a large amount of learning data is prepared by a work of adding annotations to pathological images, and this work of adding the annotations requires a lot of time and workers. In a case where a sufficient amount of learning data has not been able to be prepared, the machine learning decreases in accuracy, and it becomes difficult to derive diagnosis support information (that is, a region to which attention is to be paid in a pathological image) with high accuracy. Furthermore, there is a framework called weakly supervised learning that does not require detailed annotation data, but there is a problem in that weakly supervised learning is less accurate than machine learning that uses detailed annotation data.

Thus, the derivation device 100 of the diagnosis support system 1 according to the first embodiment derives diagnosis support information by using viewing history information regarding a region of a pathological image viewed by a pathologist at the time of pathological diagnosis. Specifically, on the basis of a first pathological image corresponding to a first affected tissue, viewing history information regarding viewing of the first pathological image by a pathologist, and diagnostic information for the affected tissue, the derivation device 100 derives diagnosis support information regarding viewing for supporting diagnosis of a second pathological image corresponding to a second affected tissue different from the first affected tissue. As described latter in detail, in a conceptual description, the derivation device 100 derives, as diagnosis support information, a region that has attracted the pathologist's attention in the first pathological image with a positive diagnosis result.

An example of processing by the derivation device 100 will be described with reference to the example in FIG. 1. In the example in FIG. 1, it is assumed that information regarding diagnosis by a pathologist is accumulated in the server 12 of the pathology system 10 on a daily basis. That is, the first pathological image, which is a pathological image corresponding to the first affected tissue, and viewing history information regarding history of viewing of the first pathological image by the pathologist are saved on the server 12. Furthermore, in the example in FIG. 1, it is assumed that the derivation device 100 provides diagnosis support information to the pathology system 20.

First, the derivation device 100 acquires, from the server 12 of the pathology system 10, the first pathological image accumulated on a daily basis and the viewing history information for the first pathological image. Furthermore, the derivation device 100 acquires, from the medical information system 30, diagnostic information regarding a diagnosis result corresponding to the first pathological image. The derivation device 100 learns the first pathological image, the viewing history information, and the diagnostic information in association with each other, thereby generating a learning model for estimating an attention region from the second pathological image corresponding to the second affected tissue different from the first affected tissue. As described latter in detail, for example, the derivation device 100 generates a learning model for estimating, as an attention region, a region of the second pathological image that is similar to a region enlarged and displayed by the pathologist, a region that has been viewed over a long time by the pathologist, or a region repeatedly viewed by the pathologist, in the first pathological image with a positive diagnosis result.

Then, it is assumed that the second pathological image corresponding to the second affected tissue is generated by the microscope 21 in the pathology system 20. At this time, when a request to display the second pathological image has been received from a user such as a doctor or a pathologist, the display control device 23 sends the second pathological image to the derivation device 100. The derivation device 100 uses the learning model to derive, from the second pathological image, diagnosis support information indicating an attention region of the second pathological image, and outputs the derived diagnosis support information to the display control device 23. The display control device 23 controls the display device 24 to display the attention region based on the diagnosis support information together with the second pathological image.

In this manner, the derivation device 100 derives information regarding an attention region as diagnosis support information on the basis of viewing history information regarding viewing of a pathological image, which is an action always performed by a pathologist at the time of pathological diagnosis. That is, the derivation device 100 uses information regarding history of viewing by a pathologist accumulated on a daily basis, and this allows for estimation of an attention region without requiring a lot of time and workers. Then, the attention region is displayed on the display device 24, and this allows the derivation device 100 to improve the accuracy of diagnosis by the pathologist with. For example, there are some cases where the diagnosis varies depending on the pathologist, but the attention region being displayed on the pathological image allows any pathologist to carefully observe the region to which attention is to be paid and make a diagnosis, and this reduces the variation in diagnosis.

Furthermore, learning by using diagnostic information allows the derivation device 100 to derive a region that has attracted attention as diagnosis support information in a case where a positive diagnosis result has been obtained. Thus, the derivation device 100 can provide a region that influences a diagnosis so as to improve the accuracy of the diagnosis.

Furthermore, in the above description, it has been described that the work of adding annotations to pathological images requires a lot of time and workers. Alternatively, the workers may perform the work of adding annotations with reference to the diagnosis support information derived by the derivation device 100. This allows for efficient generation of annotated pathological images, and machine learning can be performed on the basis of a large amount of learning data.

Note that the above description shows an example in which a learning model is generated by using, as learning data, a pathological image saved on the server 12 of the pathology system 10. Alternatively, the derivation device 100 may generate a learning model by using, as learning data, a pathological image saved on the server 22 of the pathology system 20, or may generate a learning model by using, as learning data, both the pathological image saved on the server 12 and the pathological image saved on the server 22. That is, the derivation device 100 can use, as learning data, any pathological image that has ever been viewed in the past. Furthermore, the above description shows an example in which the derivation device 100 provides diagnosis support information to the display control device 23. Alternatively, the derivation device 100 may provide diagnosis support information to the display control device 13.

Furthermore, in the above example, the pathology system 10 and the pathology system 20 have been separately described, but the pathology system 10 and the pathology system 20 may be the same system. More specifically, the diagnosis support system 1 may include only the pathology system 10. In this case, the derivation device 100 generates a learning model from the first pathological image saved on the server 12, and provides diagnosis support information to the display control device 13 in response to a request from the display control device 13. Furthermore, the number of pathology systems included in the diagnosis support system 1 may be three or more. In this case, the derivation device 100 may gather pathological images accumulated in each pathology system to generate a learning model. Furthermore, in the above example, the medical information system 30 may be the same system as the pathology system 10 or 20. That is, diagnostic information may be saved on the server 12 or 22.

The diagnosis support system 1 has been briefly described above. Hereinafter, the configuration and processing of each device will be described in detail. First, as a premise of that description, various types of information (data structure of a pathological image, viewing history information of a pathological image, and diagnostic information) will be described. Note that the following description shows an example in which the derivation device 100 performs learning by using learning data accumulated in the pathology system 10 and provides diagnosis support information to the pathology system 20.

2. Various Types of Information

[2-1. Pathological Image]

Figure 2:
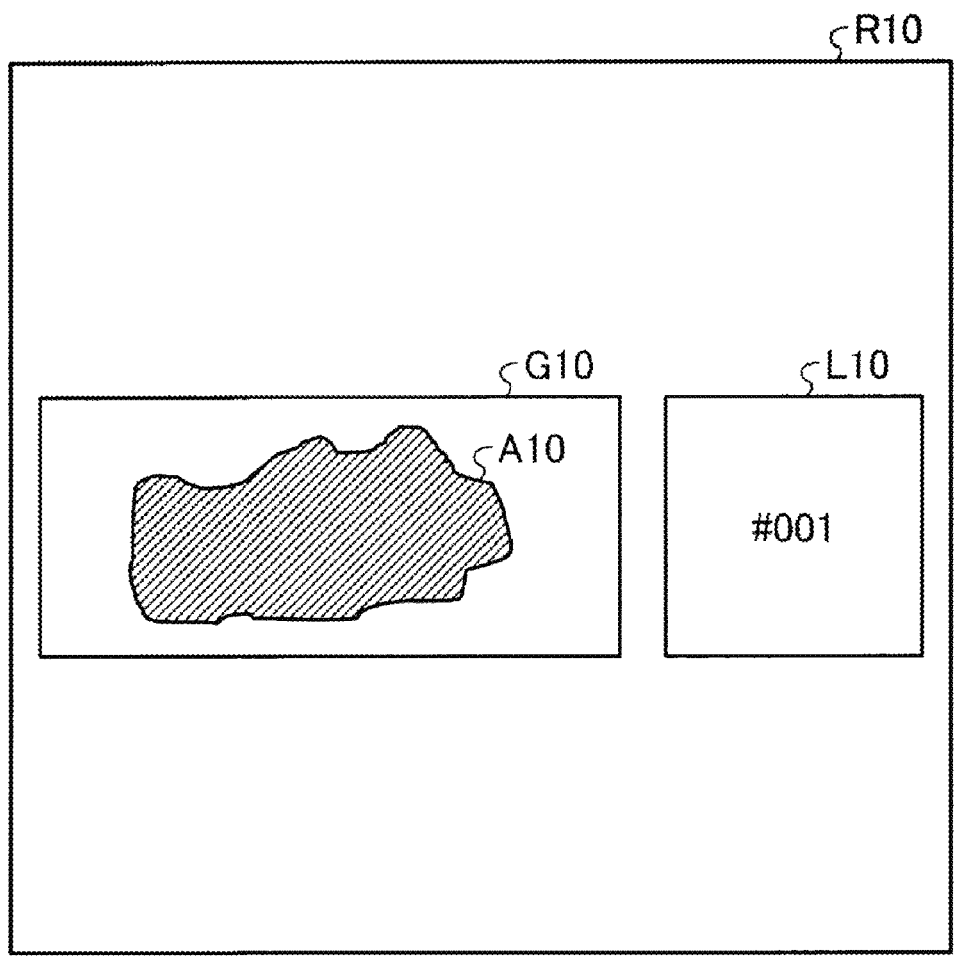
FIG. 2 is a diagram for illustrating imaging processing according to the first embodiment.
Figure 3:
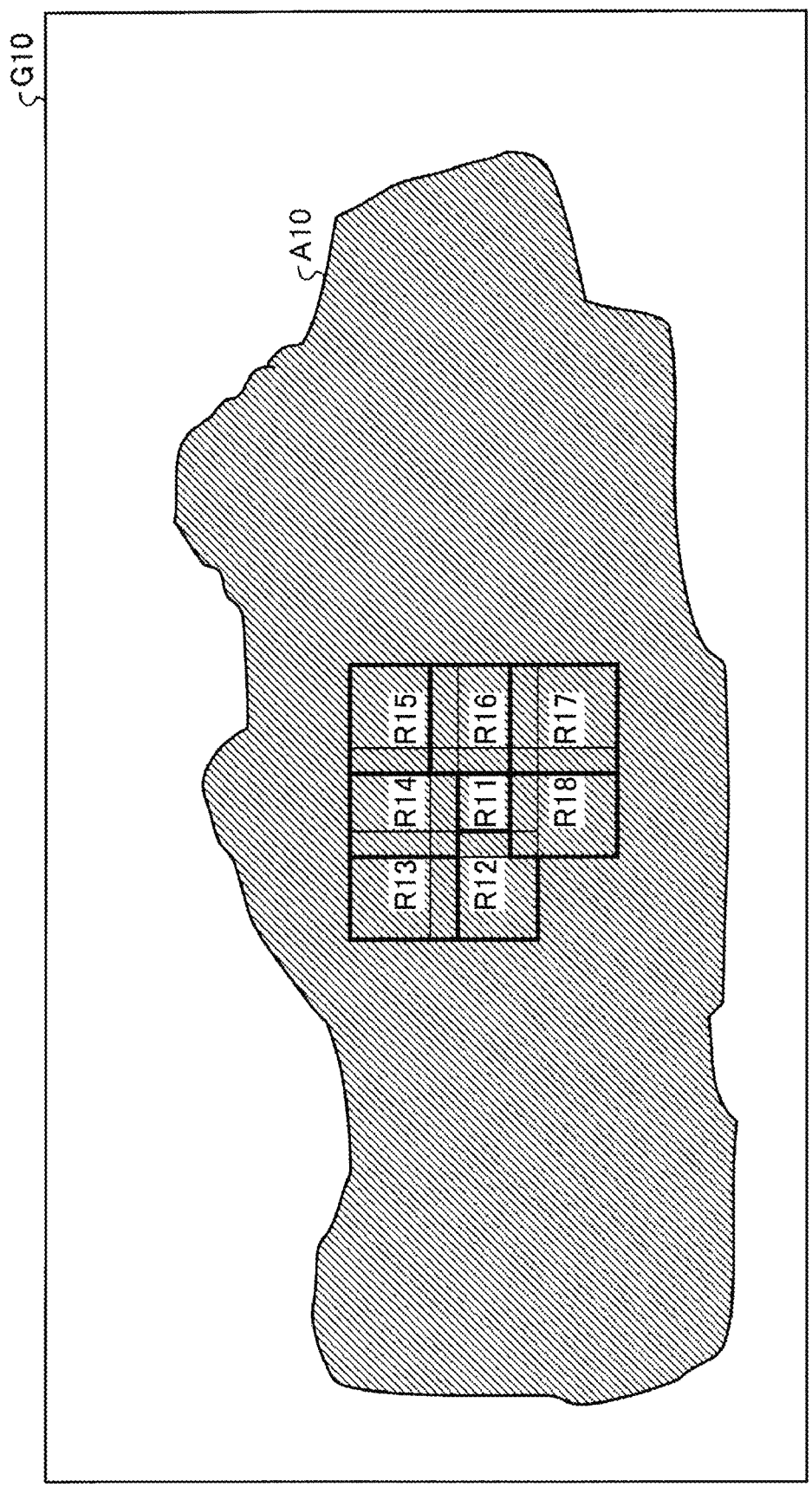
FIG. 3 is a diagram for illustrating the imaging processing according to the first embodiment.

As described above, a pathological image is generated by imaging an observation target with the microscope 11 or the microscope 21. First, imaging processing by the microscope 11 or the microscope 21 will be described with reference to FIGS. 2 and 3. FIGS. 2 and 3 are diagrams for illustrating the imaging processing according to the first embodiment. The microscope 11 and the microscope 21 perform similar imaging processing, and the microscope 11 will be described here as an example. The microscope 11 described below has a low-resolution imaging unit for imaging at low resolution and a high-resolution imaging unit for imaging at high resolution.

In FIG. 2, a glass slide G10 containing an observation target A10 is included in an imaging region R10, which is a region that can be imaged by the microscope 11. The glass slide G10 is placed on a stage (not illustrated), for example. The microscope 11 images the imaging region R10 with the low-resolution imaging unit to generate an entire image, which is a pathological image in which the entire observation target A10 has been imaged. A label information L10 illustrated in FIG. 2 contains identification information (e.g., a character string or a QR code (registered trademark)) for identifying the observation target A10. The identification information contained in the label information L10 is associated with a patient so that the patient corresponding to the entire image can be specified. In the example in FIG. 2, "#001" is shown as identification information. Note that the label information L10 may contain, for example, a brief description of the observation target A10.

Next, after generating the entire image, the microscope 11 specifies a region, in the entire image, where the observation target A10 exists, and uses the high-resolution imaging unit to sequentially image divided regions, each having a predetermined size, obtained by dividing the region where the observation target A10 exists. For example, as illustrated in FIG. 3, the microscope 11 first images a region R11, and generates a high-resolution image I11, which is an image indicating a partial region of the observation target A10. Next, the microscope 11 moves the stage to image a region R12 with the high-resolution imaging unit, and generates a high-resolution image I12 corresponding to the region R12. In a similar manner, the microscope 11 generates high-resolution images I13, I14, . . . corresponding to regions R13, R14, . . . . Although only up to a region R18 is illustrated in FIG. 3, the microscope 11 sequentially moves the stage to capture all divided regions corresponding to the observation target A10 with the high-resolution imaging unit, and generates a high-resolution image corresponding to each divided region.

Incidentally, when the stage is moved, the glass slide G10 may move on the stage. When the glass slide G10 moves, there is a possibility that a region in the observation target A10 fails to be imaged. As illustrated in FIG. 3, the microscope 11 captures an image with the high-resolution imaging unit such that adjacent divided regions partially overlap each other, and this prevents occurrence of a region that fails to be imaged even in a case where the glass slide G10 moves.

Note that the low-resolution imaging unit and the high-resolution imaging unit described above may be different optical systems, or may be the same optical system. In the case of the same optical system, the microscope 11 changes a resolution in accordance with an imaging target. Furthermore, the above description shows an example in which the imaging region is changed by moving the stage. Alternatively, the imaging region may be changed by the microscope 11 moving an optical system (high-resolution imaging unit or the like). Furthermore, FIG. 3 illustrates an example in which the microscope 11 captures an image, starting from a central portion of the observation target A10. Alternatively, the microscope 11 may image the observation target A10 in an order different from the imaging order illustrated in FIG. 3. For example, the microscope 11 may capture an image, starting from an outer peripheral portion of the observation target A10. Furthermore, the above description shows an example in which only the region where the observation target A10 exists is imaged by the high-resolution imaging unit. Alternatively, since there are some cases where the region where the observation target A10 exists cannot be accurately detected, the microscope 11 may divide the entire region of the imaging region R10 or the glass slide G10 illustrated in FIG. 2 and image the divided regions with the high-resolution imaging unit.

Figure 4:
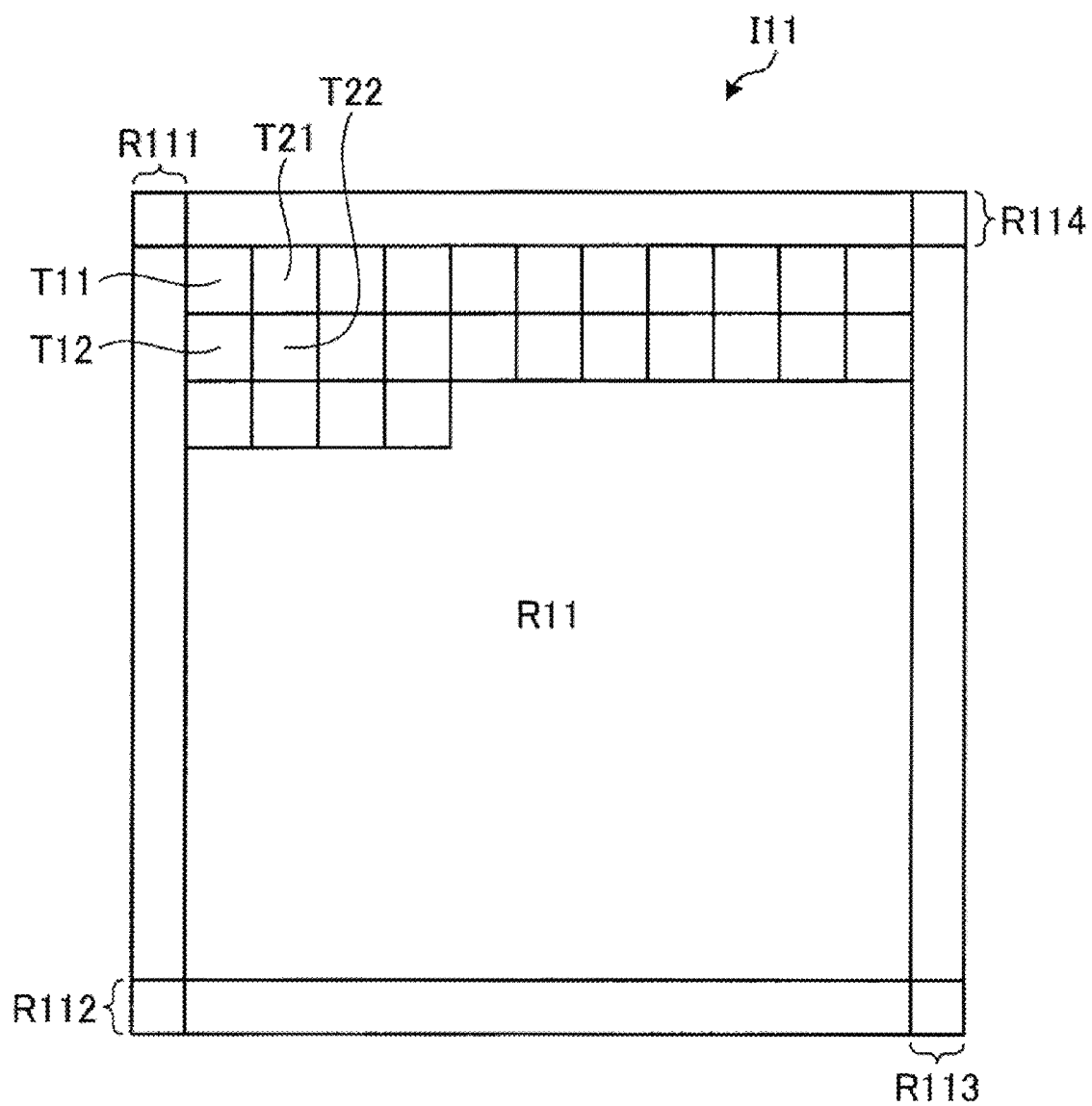
FIG. 4 is a diagram for illustrating processing of generating a partial image (tile image).

Next, each high-resolution image generated by the microscope 11 is divided into pieces of a predetermined size. As a result, partial images (hereinafter referred to as tile images) are generated from the high-resolution image. This point will be described with reference to FIG. 4. FIG. 4 is a diagram for illustrating processing of generating partial images (tile images). FIG. 4 illustrates the high-resolution image I11 corresponding to the region R11 illustrated in FIG. 3. Note that, in the following description, it is assumed that partial images are generated from a high-resolution image by the server 12. Alternatively, partial images may be generated by a device (e.g., an information processing device mounted inside the microscope 11) other than the server 12.

In the example illustrated in FIG. 4, the server 12 divides one high-resolution image I11 to generate 100 tile images T11, T12, . . . . For example, in a case where the high-resolution image I11 has a resolution of 2560×2560 [pixels], the server 12 generates 100 tile images T11, T12, . . . having a resolution of 256×256 [pixels] from the high-resolution image I11. In a similar manner, the server 12 generates tile images by dividing other high-resolution images into pieces of similar sizes.

Note that, in the example in FIG. 4, regions R111, R112, R113, and R114 are overlapped with other adjacent high-resolution images (not illustrated in FIG. 4). The server 12 adjusts positions of the overlapped regions by a technique such as template matching to perform stitching processing on high-resolution images that are adjacent to each other. In this case, the server 12 may generate tile images by dividing a high-resolution image after stitching processing. Alternatively, the server 12 may generate tile images of regions other than the regions R111, R112, R113, and R114 before stitching processing, and generate tile images of the regions R111, R112, R113, and R114 after the stitching processing.

Figure 5:
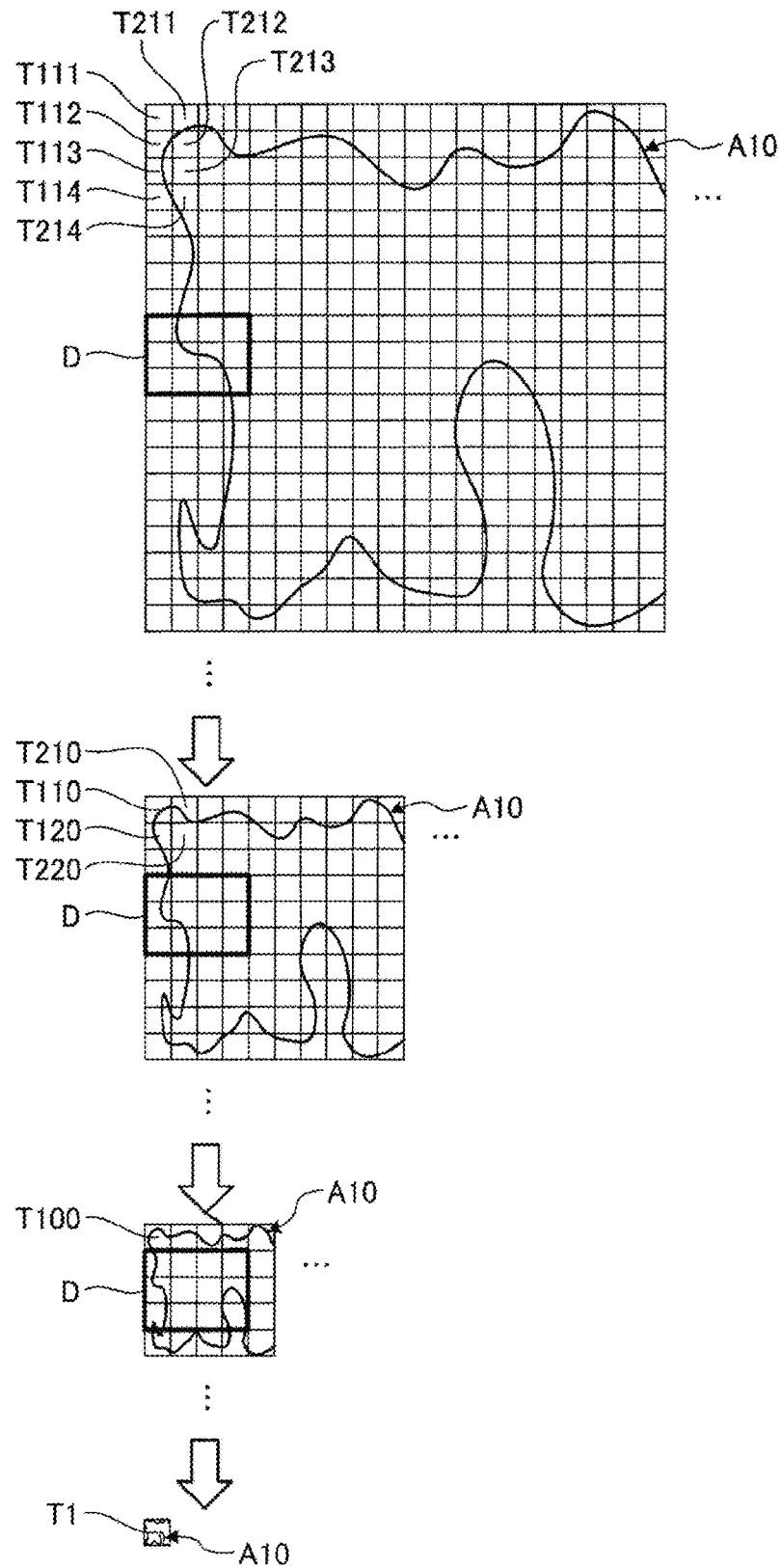
FIG. 5 is a diagram for illustrating a pathological image according to the first embodiment.
Figure 6:
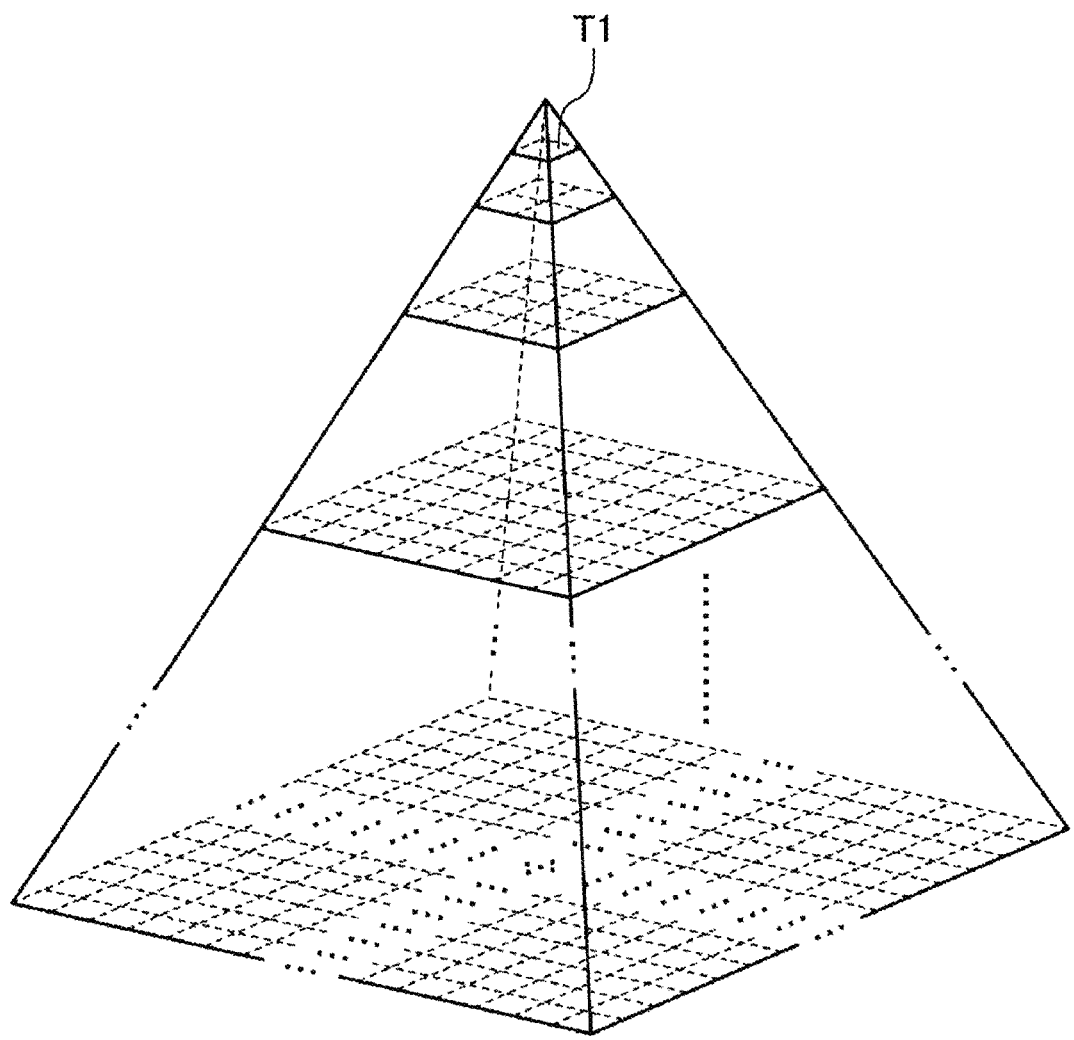
FIG. 6 is a diagram for illustrating the pathological image according to the first embodiment.

In this manner, the server 12 generates tile images, which are a minimum unit of a captured image of the observation target A10. Then, the server 12 sequentially combines the tile images in the minimum unit to generate tile images at different hierarchical levels. Specifically, the server 12 generates one tile image by combining a predetermined number of adjacent tile images. This point will be described with reference to FIGS. 5 and 6. FIGS. 5 and 6 are diagrams for illustrating a pathological image according to the first embodiment.

An upper part of FIG. 5 illustrates a group of tile images in the minimum unit generated from each high-resolution image by the server 12. In the example in the upper part of FIG. 5, the server 12 generates one tile image T110 by combining four tile images T111, T112, T211, and T212 adjacent to each other among the tile images. For example, in a case where each of the tile images T111, T112, T211, and T212 has a resolution of 256×256, the server 12 generates the tile image T110 having a resolution of 256×256. In a similar manner, the server 12 generates a tile image T120 by combining four tile images T113, T114, T213, and T214 adjacent to each other. In this manner, the server 12 generates a tile image obtained by combining a predetermined number of tile images in the minimum unit.

Furthermore, the server 12 generates a tile image obtained by further combining tile images adjacent to each other among the tile images obtained by combining the tile images in the minimum unit. In the example in FIG. 5, the server 12 generates one tile image T100 by combining four tile images T110, T120, T210, and T220 adjacent to each other. For example, in a case where the tile images T110, T120, T210, and T220 have a resolution of 256×256, the server 12 generates the tile image T100 having a resolution of 256×256. For example, the server 12 generates a tile image having a resolution of 256×256 from an image having a resolution of 512×512 obtained by combining four tile images adjacent to each other by performing four-pixel averaging, weighted filtering (processing of reflecting closer pixels more strongly than farther pixels), culling-by-half processing, or the like.

By repeating such combining processing, the server 12 finally generates one tile image having a resolution similar to the resolution of the tile images in the minimum unit. For example, as in the above example, in a case where the tile images in the minimum unit have the resolution of 256×256, the server 12 repeats the combining processing described above and finally generates one tile image T1 having the resolution of 256×256.

FIG. 6 schematically illustrates the tile images illustrated in FIG. 5. In the example illustrated in FIG. 6, a tile image group at a lowermost level is tile images in the minimum unit generated by the server 12.

Furthermore, a tile image group at the second hierarchical level from the bottom is tile images obtained by combining the tile image group at the lowermost level. Then, the tile image T1 at an uppermost level indicates one tile image that is finally generated. In this manner, the server 12 generates, as a pathological image, a tile image group having a hierarchy like a pyramid structure illustrated in FIG. 6.

Note that a region D illustrated in FIG. 5 shows an example of a region displayed on a display screen of the display device 14 or 24, or the like. For example, it is assumed that the resolution that can be displayed by the display device is three tile images in the vertical direction and four tile images in the horizontal direction. In this case, as in the region D illustrated in FIG. 5, the level of detail of the observation target A10 displayed on the display device varies depending on the hierarchical level to which the tile images to be displayed belong. For example, in a case where the tile images at the lowermost level are used, a small region of the observation target A10 is displayed in detail. Furthermore, as the level of the tile images used is higher, the displayed region of the observation target A10 is larger and grainier.

The server 12 stores the tile images at each hierarchical level as illustrated in FIG. 6 in a storage unit (not illustrated). For example, the server 12 stores each tile image together with tile identification information (an example of partial image information) that allows for unique identification of each tile image. In this case, in a case where a request to acquire a tile image that includes tile identification information has been received from another device (e.g., the display control device 13 or the derivation device 100), the server 12 transmits the tile image corresponding to the tile identification information to the other device.

Furthermore, for example, the server 12 may store each tile image together with hierarchy identification information for identifying each hierarchical level and tile identification information that allows for unique identification at the same hierarchical level. In this case, in a case where a request to acquire a tile image that includes hierarchy identification information and tile identification information has been received from another device, the server 12 transmits, to the other device, the tile image corresponding to the tile identification information among tile images belonging to a hierarchical level corresponding to the hierarchy identification information.

Note that the server 12 may store, in a storage device other than the server 12, tile images at each hierarchical level as illustrated in FIG. 6. For example, the server 12 may store tile images at each hierarchical level in a cloud server or the like. Furthermore, the processing of generating tile images illustrated in FIGS. 5 and 6 may be executed by a cloud server or the like.

Furthermore, the server 12 may not store the tile images at all the hierarchical levels. For example, the server 12 may store only the tile images at the lowermost level, may store only the tile images at the lowermost level and the tile image at the uppermost level, or may store only the tile images at a predetermined hierarchical level (e.g., odd-numbered hierarchical levels or even-numbered hierarchical levels). At this time, in a case where a tile image at a hierarchical level that has not been stored is requested from another device, the server 12 generates the tile image requested by the other device by dynamically combining stored tile images. In this manner, the server 12 can prevent a storage capacity from running out of space by culling tile images to be saved.

Furthermore, although imaging conditions have not been mentioned in the above example, the server 12 may store the tile images at each hierarchical level as illustrated in FIG. 6 for each imaging condition. Examples of the imaging conditions include a focal length to a subject (such as the observation target A10). For example, the microscope 11 may capture images while changing the focal length to the same subject. In this case, the server 12 may store tile images at each hierarchical level as illustrated in FIG. 6 for each focal length. Note that the focal length is changed because, since there are some observation targets A10 that are translucent, there is a focal length suitable for imaging the surface of the observation target A10 or a focal length suitable for imaging the inside of the observation target A10. In other words, the microscope 11 can change the focal length to generate a pathological image obtained by imaging the surface of the observation target A10 or a pathological image obtained by imaging the inside of the observation target A10.

Furthermore, another example of the imaging conditions is a staining condition for the observation target A10. To put it in specific terms, in a pathological diagnosis, a light-emitting material may be used for staining a specific portion (e.g., a cell nucleus) of the observation target A10. The light-emitting material is, for example, a material that emits light when the material is irradiated with light of a specific wavelength. Then, different light-emitting materials may be used for staining the same observation target A10. In this case, the server 12 may store the tile images at each hierarchical level as illustrated in FIG. 6 for each light-emitting material used for the staining.

Furthermore, the number and resolution of the tile images described above are merely examples, and can be changed as appropriate depending on the system. For example, the number of tile images combined by the server 12 is not limited to four. For example, the server 12 may repeat processing of combining 3×3=9 tile images. Furthermore, the above example shows an example in which the tile images have the resolution of 256×256, but the tile images may have a resolution other than 256×256.

By using software that adopts a system supporting a tile image group having the hierarchical structure described above, the display control device 13 extracts a desired tile image from a tile image group having the hierarchical structure in accordance with an input operation of a user via the display control device 13, and outputs the extracted tile image to the display device 14. Specifically, the display device 14 displays an image of an optional portion selected by the user among images having an optional resolution selected by the user. Such processing allows the user to obtain a feeling as if the user is observing the observation target while changing an observation magnification. That is, the display control device 13 functions as a virtual microscope. The virtual observation magnification here actually corresponds to the resolution.

[2-2. Viewing History Information]

Figure 7:
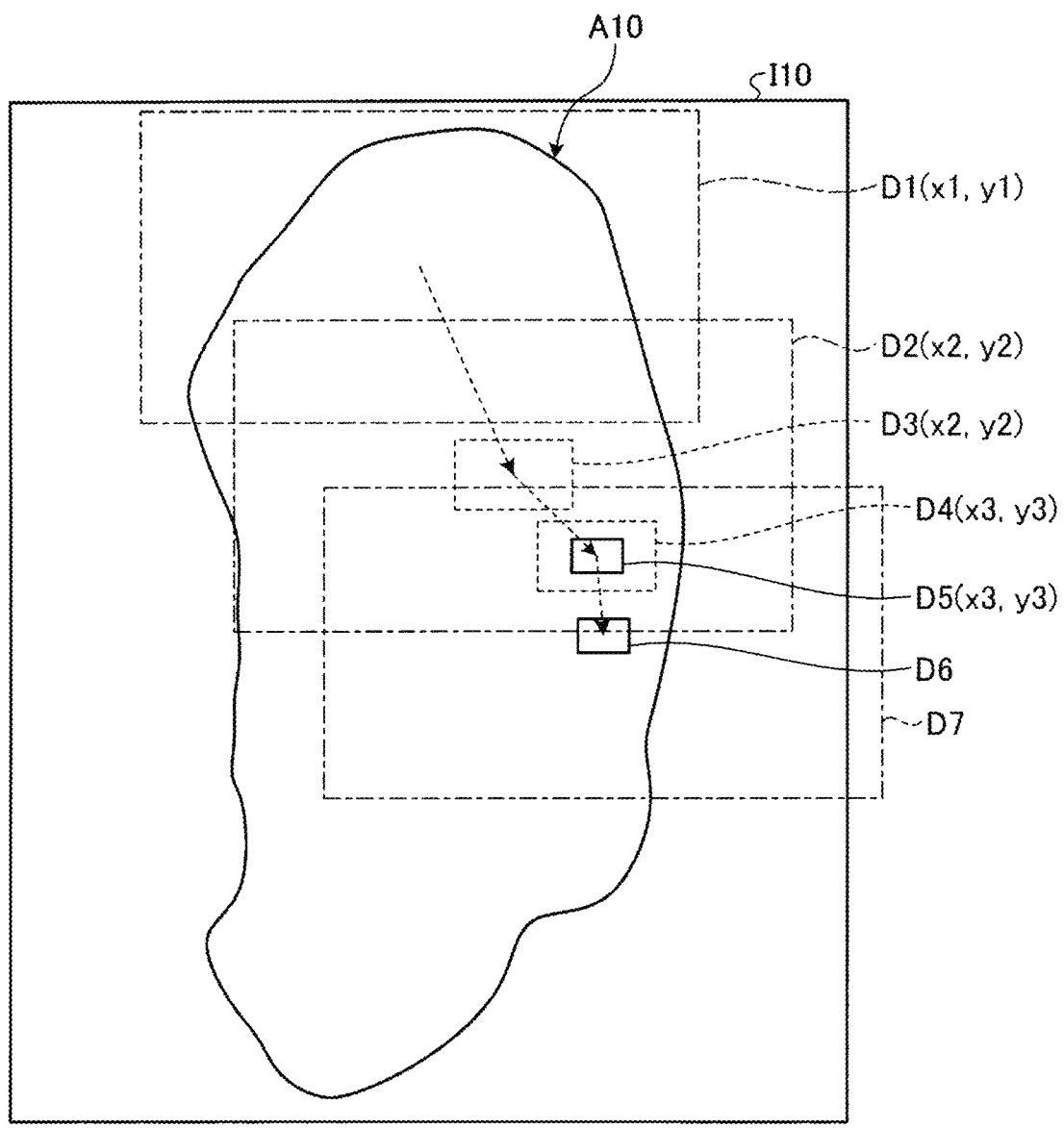
FIG. 7 is a diagram illustrating an example of a mode of viewing the pathological image by a viewer.

Next, viewing history information of a pathological image saved on the server 12 or 22 will be described with reference to FIG. 7. FIG. 7 is a diagram illustrating an example of a mode of viewing the pathological image by a viewer. In the example illustrated in FIG. 7, it is assumed that a viewer such as a pathologist has viewed regions D1, D2, D3, ..., and D7 in this order in a pathological image I10. In this case, the display control device 13 first acquires a pathological image corresponding to the region D1 from the server 12 in accordance with a viewing operation by the viewer. In response to a request from the display control device 13, the server 12 acquires, from the storage unit, one or more tile images that constitute the pathological image corresponding to the region D1, and transmits the acquired one or more tile images to the display control device 13. Then, the display control device 13 causes the display device 14 to display the pathological image constituted by the one or more tile images acquired from the server 12. For example, in a case where there is a plurality of tile images, the display control device 13 causes the plurality of tile images to be displayed side by side. In a similar manner, every time the viewer performs an operation of changing a display region, the display control device 13 acquires a pathological image corresponding to a region to be displayed (such as the region D2, D3, ..., or D7) from the server 12, and displays the acquired pathological image on the display device 14.

In the example in FIG. 7, the viewer first views the region D1, which is relatively large. A region to be carefully observed is not found in the region D1, and the viewer moves a viewing region to the region D2. Then, a region to be carefully observed has been found in the region D2, and the viewer enlarges a partial region of the region D2 and views the region D3. Then, the viewer further moves to the region D4, which is a partial region of the region D2. Then, a region to be observed more carefully has been found in the region D4, and the viewer enlarges a partial region of the region D4 and views the region D5. In this manner, the viewer also views the regions D6 and D7. For example, the pathological images corresponding to the regions D1, D2, and D7 are images displayed at a 1.25-fold magnification, the pathological images corresponding to the regions D3 and D4 are images displayed at a 20-fold magnification, and the pathological images corresponding to the regions D5 and D6 are images displayed at a 40-fold magnification. The display control device 13 acquires and displays the tile images at a hierarchical level corresponding to each magnification in the tile image group of the hierarchical structure stored in the server 12. For example, the tile images corresponding to the regions D1 and D2 are at a hierarchical level higher (that is, a hierarchical level close to the tile image T1 illustrated in FIG. 6) than the hierarchical level of the tile images corresponding to the region D3.

While a pathological image is being viewed as described above, the display control device 13 acquires viewing information at a predetermined sampling period. Specifically, the display control device 13 acquires center coordinates and a display magnification of the viewed pathological image at each predetermined timing, and stores the acquired viewing information in the storage unit of the server 12.

This point will be described with reference to FIG. 8. FIG. 8 is a diagram illustrating an example of a viewing history storage unit 12a included in the server 12. As illustrated in FIG. 8, the viewing history storage unit 12a stores information such as "sampling", "center coordinates", "magnification", and "time". The "sampling" indicates an order of timings at which viewing information is stored. The "center coordinates" indicate position information of a viewed pathological image. In this example, the center coordinates are coordinates indicated by a center position of the viewed pathological image, and correspond to coordinates of a coordinate system of a tile image group at a lowermost level. The "magnification" indicates a display magnification of the viewed pathological image. The "time" indicates a time elapsed since the start of viewing. The example in FIG. 8 indicates that the sampling period is 30 seconds. That is, the display control device 13 saves viewing information on the viewing history storage unit 12a every 30 seconds. However, this example is not restrictive, and the sampling period may be, for example, 0.1 to 10 seconds, or may be out of this range.

In the example in FIG. 8, sampling "1" indicates viewing information of the region D1 illustrated in FIG. 7, sampling "2" indicates viewing information of the region D2, samplings "3" and "4" indicate viewing information of the region D3, sampling "5" indicates viewing information of the region D4, and samplings "6", "7", and "8" indicate viewing information of the region D5. That is, the example in FIG. 8 indicates that the region D1 has been viewed for about 30 seconds, the region D2 has been viewed for about 30 seconds, the region D3 has been viewed for about 60 seconds, the region D4 has been viewed for about 30 seconds, and the region D5 has been viewed for about 90 seconds. In this manner, a viewing time of each region can be extracted from the viewing history information.

Furthermore, the number of times each region has been viewed can be extracted from the viewing history information. For example, it is assumed that the number of times of display of each pixel in a displayed pathological image is increased by one every time an operation of changing the display region (e.g., an operation of moving the display region or an operation of changing a display size) is performed. For example, in the example illustrated in FIG. 7, in a case where the region D1 is displayed first, the number of times of display of each pixel included in the region D1 becomes one. In a case where the region D2 is displayed next, the number of times of display of each pixel included in both the region D1 and the region D2 becomes two, and the number of times of display of each pixel included in the region D2 but not included in the region D1 becomes one. It is possible to specify the display region by referring to the center coordinates and the magnification in the viewing history storage unit 12a, and it is therefore possible to extract the number of times each pixel (which can also be referred to as each coordinate) in the pathological image is displayed by analyzing the viewing history information stored in the viewing history storage unit 12a.

In a case where an operation of changing a display position has not been performed by a viewer for a predetermined time (e.g., five minutes), the display control device 13 may suspend the processing of storing the viewing information. Furthermore, the above example shows an example in which the viewed pathological image is stored as viewing information on the basis of the center coordinates and the magnification, but this example is not restrictive. The viewing information may be any information as long as the information specifies the region of the viewed pathological image. For example, the display control device 13 may store, as viewing information of a pathological image, tile identification information for identifying tile images corresponding to the viewed pathological image or information indicating the position of the tile images corresponding to the viewed pathological image. Furthermore, although not illustrated in FIG. 8, information for identifying a patient, a medical record, and the like is stored in the viewing history storage unit 12a. That is, the viewing history storage unit 12a illustrated in FIG. 8 can store the viewing information in association with the patient, the medical record, and the like.

[2-3. Diagnostic Information]

Next, diagnostic information stored in the medical information system 30 will be described with reference to FIGS. 9A to 9C. FIGS. 9A to 9C are diagrams illustrating a diagnostic information storage unit included in the medical information system 30. FIGS. 9A to 9C illustrate examples in which diagnostic information is stored in different tables for each organ to be examined. For example, FIG. 9A illustrates an example of a table storing diagnostic information regarding a breast cancer examination, FIG. 9B illustrates an example of a table storing diagnostic information regarding a lung cancer examination, and FIG. 9C illustrates an example of a table storing diagnostic information regarding an examination of large intestine.

A diagnostic information storage unit 30A illustrated in FIG. 9A stores information such as "patient ID", "pathological image", "diagnosis result", "grade", "tissue type", "genetic testing", "ultrasonography", and "medication". The "patient ID" indicates identification information for identifying a patient. The "pathological image" indicates a pathological image saved by a pathologist at the time of diagnosis. The "pathological image" stored may be, instead of the image itself, position information (center coordinates, magnification, and the like) indicating an image region to be saved with respect to the entire image. The "diagnosis result" is a result of a diagnosis by a pathologist, and indicates, for example, whether a lesion site has been found and a type of the lesion site. The "grade" indicates a degree of progression of a diseased site. The "tissue type" indicates a type of diseased site. The "genetic testing" indicates a result of a genetic testing. The "ultrasonography" indicates a result of ultrasonography. Medication indicates information regarding medicine given to the patient.

A diagnostic information storage unit 30B illustrated in FIG. 9B stores information regarding "computed tomography examination" performed in a lung cancer examination, instead of "ultrasonography" stored in the diagnostic information storage unit 30A illustrated in FIG. 9A. A diagnostic information storage unit 30C illustrated in FIG. 9C stores information regarding "endoscopic examination" performed in an examination of large intestine instead of "ultrasonography" stored in the diagnostic information storage unit 30A illustrated in FIG. 9A.

In the examples in FIGS. 9A to 9C, in a case where "normal" is stored in "diagnosis result", it indicates that the result of the pathological diagnosis is negative. In a case where information other than "normal" is stored in "diagnosis result", it indicates that the result of the pathological diagnosis is positive.

3. Device Configuration

[3-1. Derivation Device According to First Embodiment]

Figure 10:
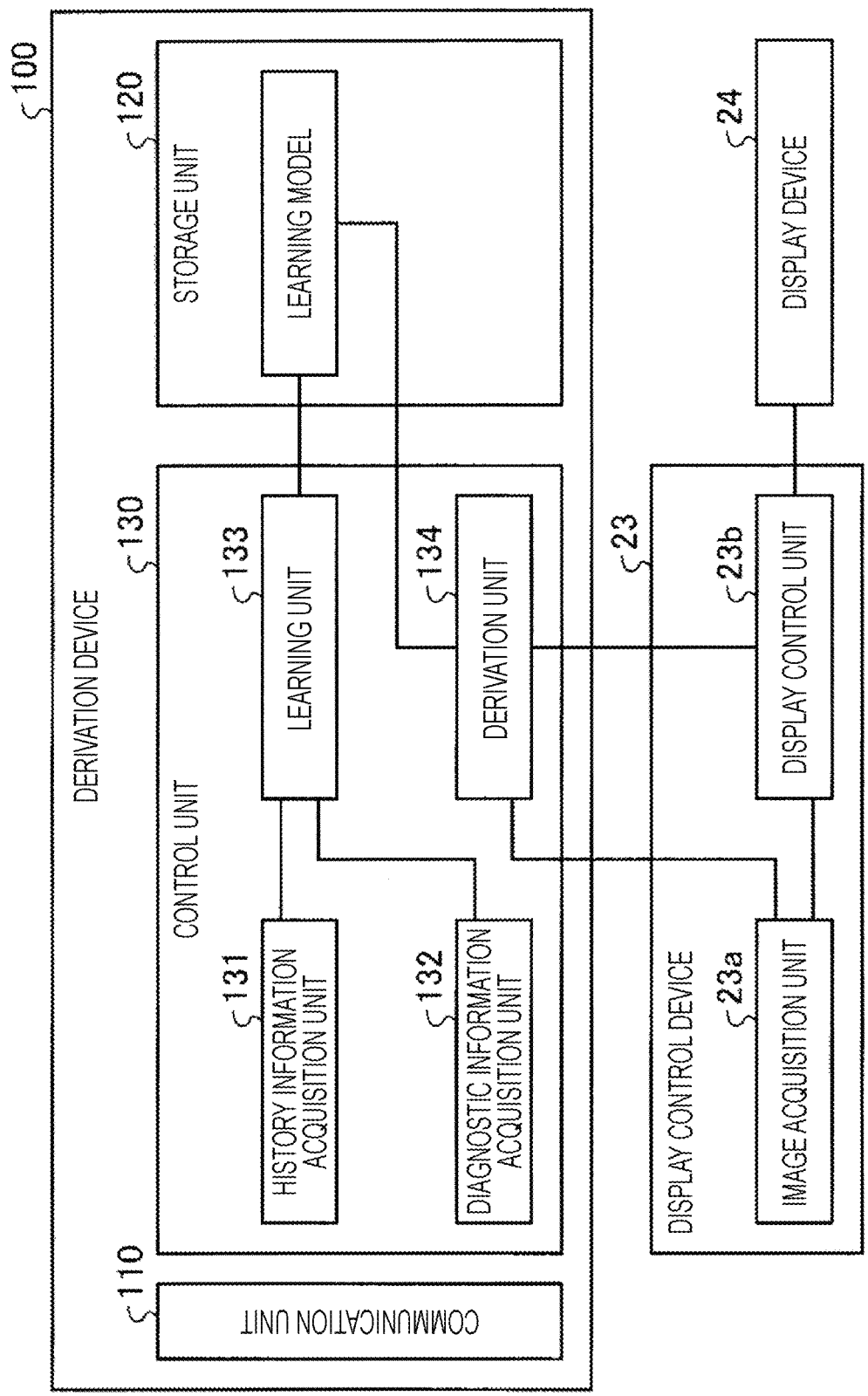
FIG. 10 is a diagram illustrating an example of a derivation device and a display control device according to the first embodiment.

Next, the derivation device 100 according to the first embodiment will be described. Here, the display control device 23 will be described together with the derivation device 100. FIG. 10 is a diagram illustrating an example of the derivation device 100 and the display control device 23 according to the first embodiment. As illustrated in FIG. 10, the derivation device 100 is a computer having a communication unit 110, a storage unit 120, and a control unit 130.

The communication unit 110 is constituted by, for example, a network interface card (NIC). The communication unit 110 is connected to a network (not illustrated) in a wired or wireless manner, and transmits and receives information to and from the pathology system 10, the pathology system 20, the medical information system 30, and the like via the network. The control unit 130 described later transmits and receives information to and from these devices via the communication unit 110.

The storage unit 120 is constituted by, for example, a semiconductor memory element such as a random access memory (RAM) or a flash memory, or a storage device such as a hard disk or an optical disk. The storage unit 120 stores a learning model 121 generated by the control unit 130. The learning model 121 will be described later.

The control unit 130 is implemented by, for example, a central processing unit (CPU) or a micro processing unit (MPU) executing a program (an example of a diagnosis support program) stored in the derivation device 100 by using a random access memory (RAM) or the like as a working area. Furthermore, the control unit 130 may be executed by an integrated circuit such as an application specific integrated circuit (ASIC) or a field programmable gate array (FPGA).

As illustrated in FIG. 10, the control unit 130 has a history information acquisition unit 131, a diagnostic information acquisition unit 132, a learning unit 133, and a derivation unit 134, and implements or executes a function or an action of the information processing described below. Note that an internal configuration of the control unit 130 is not limited to the configuration illustrated in FIG. 10, and may be any other configuration that performs information processing described later.

The history information acquisition unit 131 acquires information used for learning processing performed by the learning unit 133 via the communication unit 110. Specifically, the history information acquisition unit 131 acquires a first pathological image corresponding to a first affected tissue and viewing history information regarding viewing of the first pathological image stored in the server 12 of the pathology system 10. As in the example illustrated in FIG. 8, the viewing history information acquired by the history information acquisition unit 131 includes information regarding a region, in the first pathological image, enlarged and viewed by a pathologist, information regarding a region, in the first pathological image, viewed over a relatively long time by the pathologist, and information regarding the number of times the pathologist has viewed each region in the first pathological image.

The diagnostic information acquisition unit 132 acquires information used for learning processing performed by the learning unit 133 via the communication unit 110. Specifically, the diagnostic information acquisition unit 132 acquires, from the medical information system 30, diagnostic information for the first affected tissue corresponding to the first pathological image.

The learning unit 133 learns an association among the first pathological image and the viewing history information acquired by the history information acquisition unit 131 and the diagnostic information acquired by the diagnostic information acquisition unit 132. As a result, the learning unit 133 generates a learning model for estimating an attention region in a second pathological image. Then, the learning unit 133 stores the learning model 121 in the storage unit 120.

The learning processing by the learning unit 133 will be described more specifically. First, the learning unit 133 generates learning data. Specifically, the learning unit 133 generates a heat map image in which information regarding the attention region is reflected in the first pathological image on the basis of the viewing history information acquired by the history information acquisition unit 131. For example, the learning unit 133 associates each pixel in the first pathological image with an index value (hereinafter referred to as an attention index value), which is larger as a viewer pays more attention.

As an example, the learning unit 133 associates a pixel having a higher display magnification with a higher attention index value. To describe using the example illustrated in FIG. 7, it is assumed that the pathological image corresponding to the region D1 is an image displayed at a 1.25-fold magnification, the pathological image corresponding to the region D3 is an image displayed at a 20-fold magnification, and the pathological image corresponding to the region D5 is an image displayed at a 40-fold magnification. In this case, the learning unit 133 sets the attention index value of each pixel included in the region D3 to be higher than the attention index value of each pixel included in the region D1. Furthermore, the learning unit 133 sets the attention index value of each pixel included in the region D5 to be higher than the attention index value of each pixel included in the region D3.

Furthermore, for example, the learning unit 133 associates a pixel having a longer viewing time with a higher attention index value. The example in FIG. 8 indicates that the region D1 has been viewed for about 30 seconds, the region D3 has been viewed for about 60 seconds, and the region D5 has been viewed for about 90 seconds. In this case, the learning unit 133 sets the attention index value of each pixel included in the region D3 to be higher than the attention index value of each pixel included in the region D1. Furthermore, the learning unit 133 sets the attention index value of each pixel included in the region D5 to be higher than the attention index value of each pixel included in the region D3.

Furthermore, for example, the learning unit 133 associates a pixel having a larger number of times of viewing with a higher attention index value. Note that the learning unit 133 may associate an attention index value by using only one of pieces of information: a magnification ratio; the viewing time; and the number of times of viewing, or may associate an attention index value by using two or more pieces of the information. In this manner, the learning unit 133 generates a heat map image in which each pixel in each first pathological image acquired by the history information acquisition unit 131 is associated with an attention index value. Note that the heat map image is, for example, a set of data that is a combination of a pixel in the first pathological image and an attention index value associated with the pixel, and can be said to be viewing history information indicated by the attention index value.

Next, the learning unit 133 performs machine learning by using, as learning data, a combination of the first pathological image, the heat map image corresponding to the first pathological image, and the diagnostic information corresponding to the first pathological image. For example, the learning unit 133 learns learning data with a positive diagnosis result (e.g., diagnosis results in the diagnostic information storage units 30A to 30C are other than "normal") as a positive example, and learning data with a negative diagnosis result (e.g., diagnosis results in the diagnostic information storage units 30A to 30C are "normal") as a negative example. The learning processing by the learning unit 133 is a black box, and will therefore be described conceptually. The learning unit 133 generates the learning model 121 that outputs a higher score (hereinafter referred to as an attention score) for a region, among regions in a new pathological image (second pathological image), having an image feature amount similar to that of a region in which the attention index value tends to be higher in a first pathological image group with a positive diagnosis result.

It can be said that the attention score for each region in the second pathological image output by the learning model 121 indicates the degree of attention paid by a pathologist in the past to a region similar to the region. Here, since the pathologist views a region containing a lesion area with more attention, it can be said that the region that has attracted the pathologist's attention is a region where there is a high possibility that a lesion area exists. That is, it can be said that the attention score output by the learning model 121 indicates a probability that a lesion area exists in the corresponding region. For example, in a case where a first pathological image for learning data has been used for a cancer examination, it can be said that the attention score of each region indicates the probability that cancer tissue exists in that region, that is, indicates a region estimated to influence a diagnosis.

Note that, in the above example, the first pathological image with a positive diagnosis result is a positive example. However, even in a case where the diagnosis result is positive, not all observation targets visualized in the first pathological image are positive, and the observation target visualized in a partial region of the first pathological image is often a lesion area. Thus, the learning unit 133 may learn, as a positive example, only a region in which the attention index value is equal to or greater than a predetermined threshold value TH1 in the first pathological image with a positive diagnosis result, and may learn, as a negative example, a region in which the attention index value is smaller than the predetermined threshold value TH1. Furthermore, the learning unit 133 may learn using only a first pathological image with a positive diagnosis result.

For example, weakly supervised learning can be applied to the learning by the learning unit 133, and the following approaches can also be used.

"WILDCAT: Weakly Supervised Learning of Deep ConvNets for Image Classification, Pointwise Localization and Segmentation", CVPR 2017
(http://webia.lip6.fr/~durandt/pdfs/2017_CVPR/Durand_WILDCAT_CVPR_2017.pdf)

"Attention-based Deep Multiple Instance Learning", 2018 (https://arxiv.org/abs/1802.04712)

However, the learning approach by the learning unit 133 may be based on any algorithm. For example, the learning unit 133 can generate a learning model by using various learning algorithms such as deep learning, support vector machine, clustering, and reinforcement learning, which are machine learning approaches based on a deep neural network.

Furthermore, the learning unit 133 may not use all the first pathological images for learning. For example, the learning unit 133 may perform learning by using only a first pathological image that has attracted particular attention. For example, the learning unit 133 may perform learning by using only a first pathological image that includes a region viewed for a predetermined time or more, may perform learning by using only a first pathological image that includes a region viewed at a predetermined magnification, or may perform learning by using only a first pathological image that includes a region viewed a predetermined number of times or more. Furthermore, for example, the learning unit 133 may perform learning by using only a region viewed for a predetermined time or more, may perform learning by using only a region viewed at a predetermined magnification, or may perform learning by using only a region viewed a predetermined number of times or more. Furthermore, for example, assuming that a center region of a first pathological image is a region that has attracted attention, the learning unit 133 may extract only the center region of the first pathological image for learning.

Furthermore, the above description shows an example in which the learning unit 133 generates a heat map image as learning data. Alternatively, the processing of generating a heat map image may be performed by the microscope 11, the server 12, or the like. Then, the heat map image may be stored in the server 12. In this case, the history information acquisition unit 131 acquires the heat map image from the server 12 as viewing history information.

The derivation unit 134 acquires a second pathological image from the display control device 23 and uses a learning model on the acquired second pathological image, thereby deriving diagnosis support information, which is information regarding viewing of the second pathological image, on the basis of an attention region of the second pathological image estimated from the viewing history information. Specifically, the derivation unit 134 derives the diagnosis support information, assuming that a region with a larger display magnification in the first pathological image is an attention region with a higher degree of attention, a region with a longer viewing time in the first pathological image is an attention region with a higher degree of attention, or a region with a larger number of times of viewing in the first pathological image is an attention region with a higher degree of attention. Then, the derivation unit 134 outputs the diagnosis support information, which is a derived result, to the display control device 23.

An example will be described. The derivation unit 134 receives, from the display control device 23, a second pathological image and a request for estimating an attention region of the second pathological image. The second pathological image is, for example, a pathological image with which a pathologist is making a diagnosis. Then, the derivation unit 134 uses the learning model 121 stored in the storage unit 120 to estimate the attention region of the second pathological image. As described above, the learning model 121 outputs a higher attention score for a region that is more similar to a region that has attracted the pathologist's attention in the pathological image with a positive diagnosis result. It can be said that such an attention score indicates the degree of importance in pathological diagnosis, that is, the degree of influence on the diagnosis. The derivation unit 134 specifies, as an attention region, a region in the second pathological image in which the attention score calculated with the use of the learning model 121 is higher than a predetermined threshold value TH2. Then, the derivation unit 134 transmits, to the display control device 23, diagnosis support information indicating position information regarding the attention region of the second pathological image. For example, the derivation unit 134 transmits, to the display control device 23, information regarding coordinates and tile images (tile identification information, or a combination of hierarchy identification information and tile identification information), as position information.

[3-2. Display Control Device According to First Embodiment]

Next, the display control device 23 will be described. The display control device 23 is equipped with a pathological image display control program for displaying a pathological image such as the tile images described above. However, this is not restrictive, and the pathological image display control program may be downloaded from a server or installed from a storage medium such as a digital versatile disc (DVD) to a general-purpose computer for the processing by the display control device 23 described below. Furthermore, the processing by the display control device 23 described below may be performed by two or more devices. For example, a part of the processing may be performed on a server, and the rest of the processing may be performed on a client computer such as the display control device 23. Furthermore, the processing by the display control device 23 described below may be performed by the pathological image display control program running on a cloud.

As illustrated in FIG. 10, the display control device 23 has an image acquisition unit 23a and a display control unit 23b, and is a computer that implements or executes a function or an action of the information processing described below. Note that an internal configuration of the display control device 23 is not limited to the configuration illustrated in FIG. 10, and may be any other configuration that performs information processing described later. Furthermore, the image acquisition unit 23a and the display control unit 23b are implemented by, for example, a CPU or an MPU executing a display control program stored in the display control device 23 by using a RAM or the like as a working area. Furthermore, the image acquisition unit 23*a* and the display control unit 23*b* may be executed by an integrated circuit such as an ASIC or an FPGA.

The image acquisition unit 23*a* acquires a second pathological image from the server 22, and transmits the acquired second pathological image to the derivation device 100. For example, the image acquisition unit 23*a* transmits the second pathological image to be diagnosed by a pathologist to the derivation device 100 in accordance with an operation by the pathologist. Note that the image acquisition unit 23*a* and the display control unit 23*b* may be the same, and the processing of transmitting the second pathological image to the derivation device 100 may be performed by the display control unit 23*b*.

The display control unit 23*b* receives diagnosis support information corresponding to the second pathological image from the derivation device 100. Then, on the basis of the diagnosis support information, the display control unit 23*b* controls the display device 24 to display the second pathological image in a state where an attention region, which is a region estimated to influence a diagnosis, is visible. Note that, in the following description, the display control unit 23*b* controlling the display device 24 so that various types of information such as a pathological image is displayed on the display device 24 may be simply referred to as the display control unit 23*b* displaying various types of information.

Figure 11:
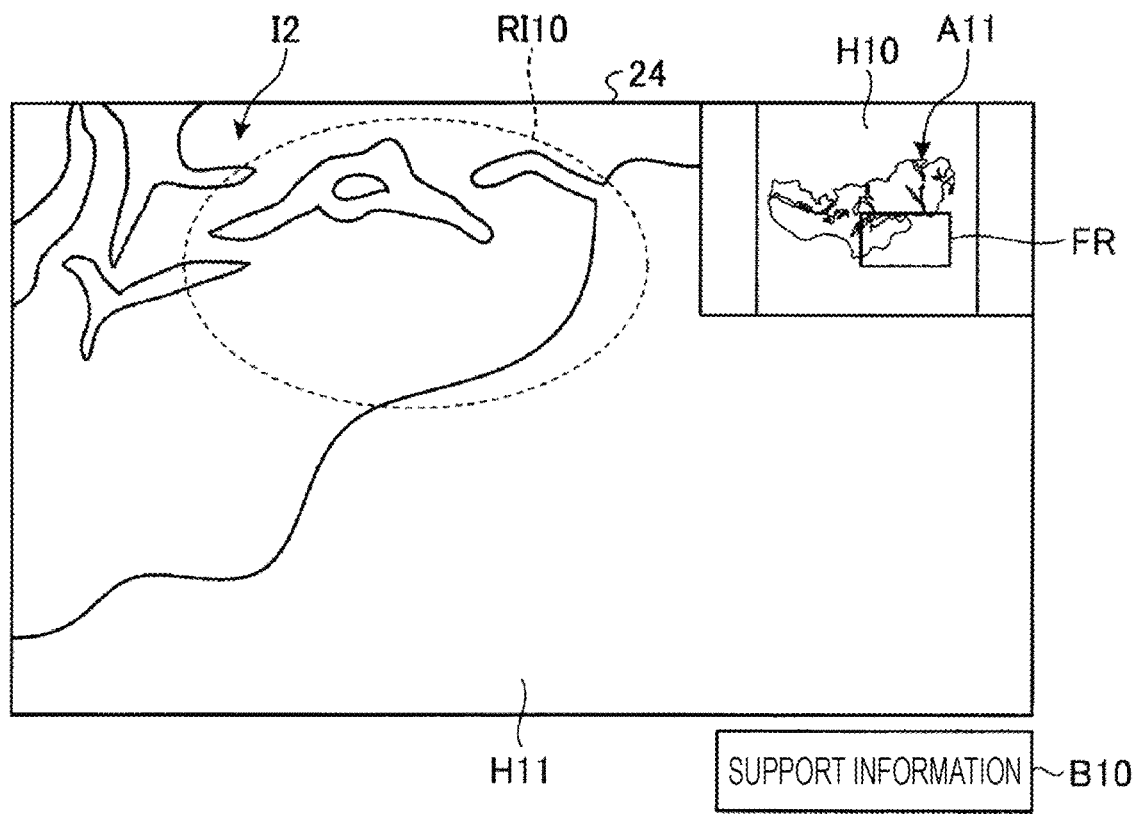
FIG. 11 is a diagram illustrating an example of displaying a pathological image by the display control device according to the first embodiment.

FIG. 11 is a diagram illustrating an example of displaying a pathological image by the display control device 23 according to the first embodiment. In the example illustrated in FIG. 11, the display control unit 23*b* displays an entire observation target A11 in an entire display region H10, enlarges and displays a partial region of the observation target A11 in an enlarged display region H11, and also displays a support information button B10. For example, the display control unit 23*b* displays, in the entire display region H10, a pathological image I1 constituted by tile images at an optional hierarchical level among the tile image group having the hierarchical structure illustrated in FIG. 6. Furthermore, the display control unit 23*b* displays, in the enlarged display region H11, a pathological image I2 constituted by tile images at a hierarchical level lower than that of the tile images displayed in the entire display region H10.

Furthermore, as illustrated in FIG. 11, the display control unit 23*b* displays, in the entire display region H10, an enlarged region frame FR indicating the region displayed in the enlarged display region H11. A viewer such as a pathologist can change the region of the observation target A11 to be displayed in the enlarged display region H11 by performing an operation of moving the enlarged region frame FR (a mouse drag operation or the like). As a result, the viewer can check a part of the observation target A11 in more detail by viewing the pathological image in the enlarged display region H11 while grasping the entire observation target A11 in the entire display region H10.

Here, when the viewer selects the support information button B10, the display control unit 23*b* visibly displays a region to which attention is to be paid in the pathological image I2 displayed in the enlarged display region H11 on the basis of diagnosis support information received from the derivation device 100. For example, the display control unit 231 acquires diagnosis support information corresponding to the pathological image I2 by transmitting the pathological image I2 displayed in the enlarged display region H11 to the derivation device 100. Then, the display control unit 23*b* displays a frame image RI10, which is a dotted outer frame surrounding a region to which attention is to be paid on the basis of the diagnosis support information acquired from the derivation device 100. This allows the viewer to determine that, in the pathological image displayed in the enlarged display region H11, the region indicated by the frame image RI10 should be observed more carefully.

Note that, when the support information button B10 is selected again while the frame image RI10 is displayed, the display control unit 23*b* may hide the frame image RI10 that has been displayed. This allows the viewer to observe the pathological image to which unnecessary information is not added.

The example in FIG. 11 shows an example in which the frame image RI10 is displayed in the enlarged display region H11. Alternatively, the display control unit 23*b* may display a frame image corresponding to the pathological image I1 in the entire display region H10 instead of the enlarged display region H11. In this case, the image acquisition unit 23*a* acquires diagnosis support information corresponding to the pathological image I1 by transmitting the pathological image I1 to the derivation device 100. This allows the viewer to make the region, in the pathological image I1, where the frame image is displayed to be displayed in the enlarged display region H11, and carefully observe all regions to which attention is to be paid in the observation target A11. Furthermore, the display control unit 23*b* may display frame images in both the entire display region H10 and the enlarged display region H11.

Furthermore, the display control device 23 may acquire diagnosis support information from the derivation device 100 in real time at the timing when a pathologist views a pathological image. Alternatively, the display control device 23 may acquire diagnosis support information in advance by periodically (e.g., once a day) transmitting a pathological image stored in the server 22 to the derivation device 100.

4. Processing Procedure

[4-1. Learning Processing Procedure According to First Embodiment]

Figure 12:
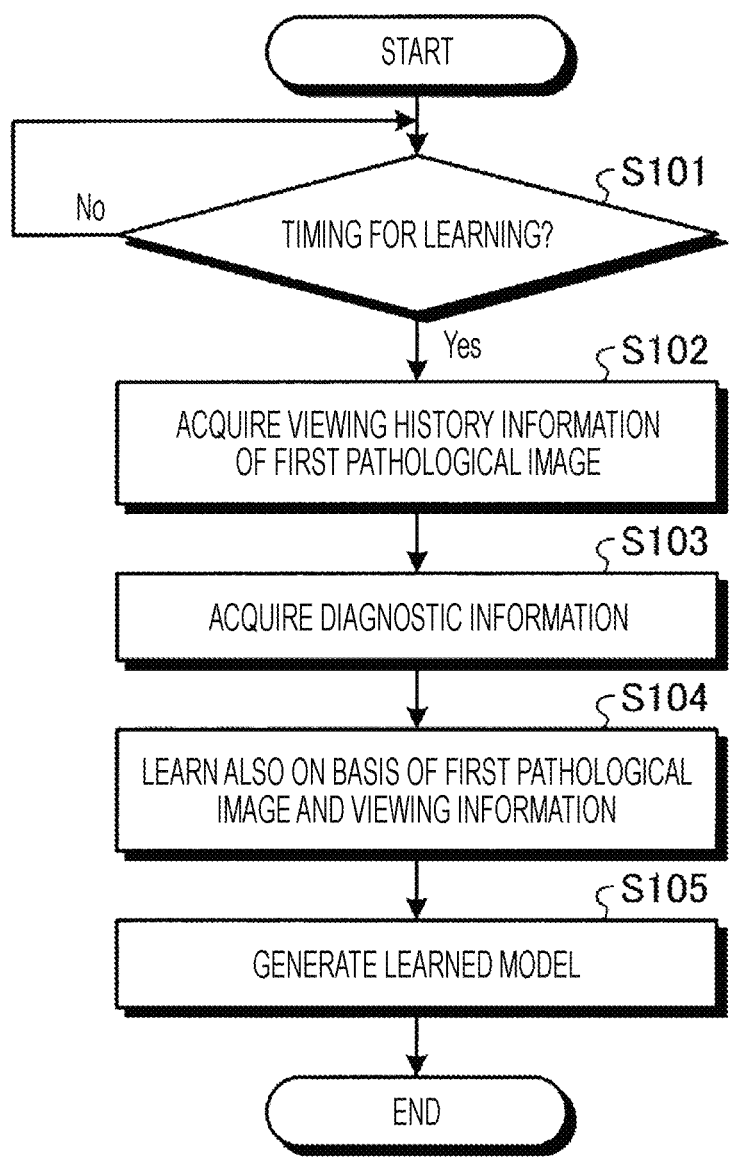
FIG. 12 is a flowchart illustrating a learning processing procedure according to the first embodiment.

Next, a processing procedure according to the first embodiment will be described with reference to FIGS. 12 and 13. FIG. 12 is a flowchart illustrating a learning processing procedure according to the first embodiment. As illustrated in FIG. 12, the derivation device 100 determines whether or not it is a timing for learning (step S101). For example, in a case where a learning date and time on which learning is to be performed has been fixed in advance, the derivation device 100 determines whether or not the current date and time is the learning date and time.

Then, if it is a timing for learning (step S101; Yes), the derivation device 100 acquires a first pathological image and viewing history information of the first pathological image from the server 12 (step S102). Furthermore, the derivation device 100 acquires, from the medical information system 30, diagnostic information corresponding to the first pathological image acquired from the server 12 (step S103).

Next, the derivation device 100 learns a relationship between a diagnosis result and a heat map image based on the viewing history information (the viewing time, the number of times of viewing, the magnification, and the like) (step S104). Thus, the derivation device 100 generates a learning model 121 (step S105). Then, the derivation device 100 stores the learning model 121 that has been learned in the storage unit 120.

Note that although FIG. 12 illustrates an example in which the learning model 121 is newly generated, there are some cases where the derivation device 100 relearns the learning model 121 that has been learned. In this case, the derivation device 100 corrects the learning model 121 by using new learning data.

[4-2. Derivation Processing Procedure According to First Embodiment]

Figure 13:
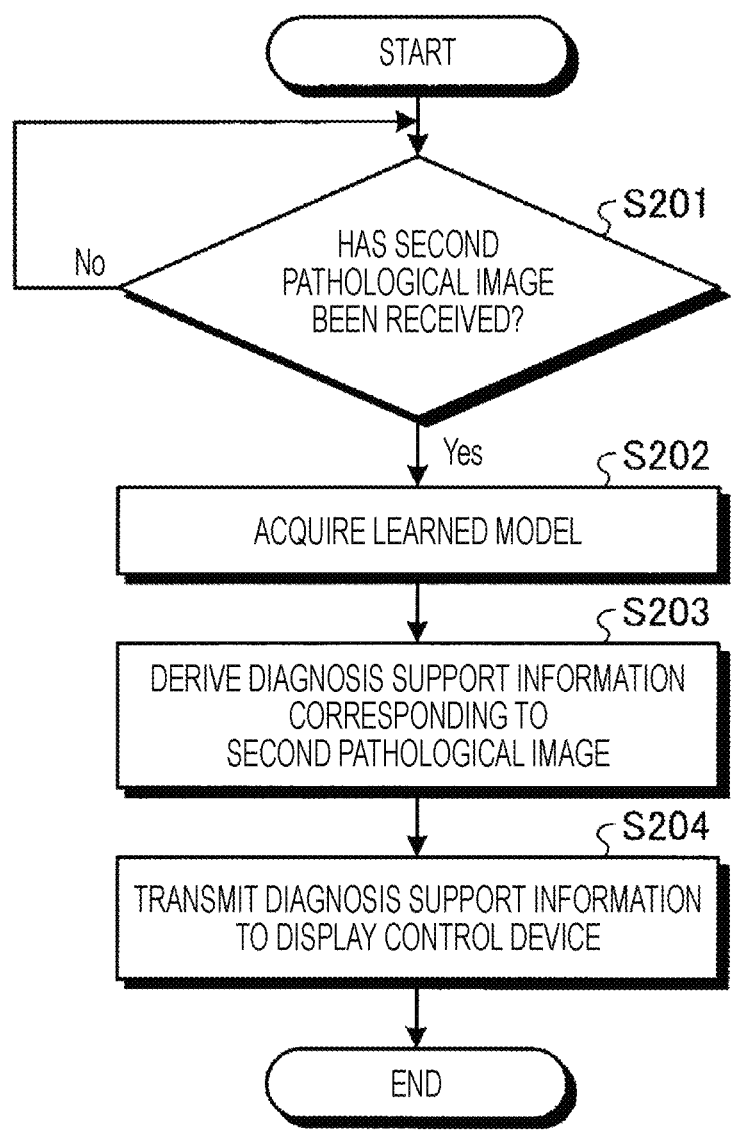
FIG. 13 is a flowchart illustrating a derivation processing procedure according to the first embodiment.

FIG. 13 is a flowchart illustrating a derivation processing procedure according to the first embodiment. As illustrated in FIG. 13, the derivation device 100 determines whether or not a second pathological image has been received from the display control device 23 (step S201).

Then, if a second pathological image has been received (step S201; Yes), the derivation device 100 acquires, from the storage unit 120, the learning model 121 that has been learned (step S202). Next, the derivation device 100 uses the learning model 121 to derive diagnosis support information, which is information indicating a region to which attention is to be paid in the second pathological image (step S203). Then, the derivation device 100 transmits the diagnosis support information to the display control device 23 (step S204). Thus, the display control device 23 controls the display device 24 to display the second pathological image together with the diagnosis support information as in the example illustrated in FIG. 11.

5. Modified Examples 1

Modified examples of the display processing will be described below with reference to FIGS. 14 to 22. FIGS. 14 to 22 are diagrams illustrating examples of displaying a pathological image according to the modified examples.

[5-1. Display Example (1)]

FIG. 11 illustrates an example in which information (frame image RI10) indicating one attention region is displayed. Alternatively, the display control unit 23b may display, for each threshold value of a plurality of attention scores, information indicating attention regions corresponding to attention scores equal to or greater than the threshold value. At this time, the display control unit 23b may change a display mode of the information indicating attention regions for each attention score. Furthermore, FIG. 11 illustrates an example in which the dotted frame image RI10 is displayed as information indicating an attention region. Alternatively, the display control unit 23b may display a mask image that translucently covers an attention region as information indicating the attention region. Furthermore, the display control unit 23b may display side by side a pathological image on which the information indicating the attention region is not superimposed and the pathological image on which the information indicating the attention region is superimposed.

This point will be described with reference to FIG. 14. In the example illustrated in FIG. 14, the display control unit 23b displays, on the left side of a display screen, a pathological image I21 without information indicating an attention region superimposed, and displays, on the right side of the display screen, the pathological image I21 with information indicating an attention region superimposed. Here, the display control unit 23b displays mask images RI11, RI12, and RI13 that are filled translucently as information indicating attention regions. Note that it is assumed that the attention score is higher in the order of the mask images RI11, RI12, and RI13. For example, the mask image RI11 is superimposed on a region in which the attention score is equal to or greater than a threshold value TH11, the mask image RI12 is superimposed on a continuous region in which the attention score is equal to or greater than a threshold value TH12 (>TH11), and the mask image RI13 is superimposed on a continuous region in which the attention score is equal to or greater than a threshold value TH13 (>TH12). The display control unit 23b may change saturation, luminance, or transmittance of the mask images RI11, RI12, and RI13 in accordance with the attention score.

Figure 14:
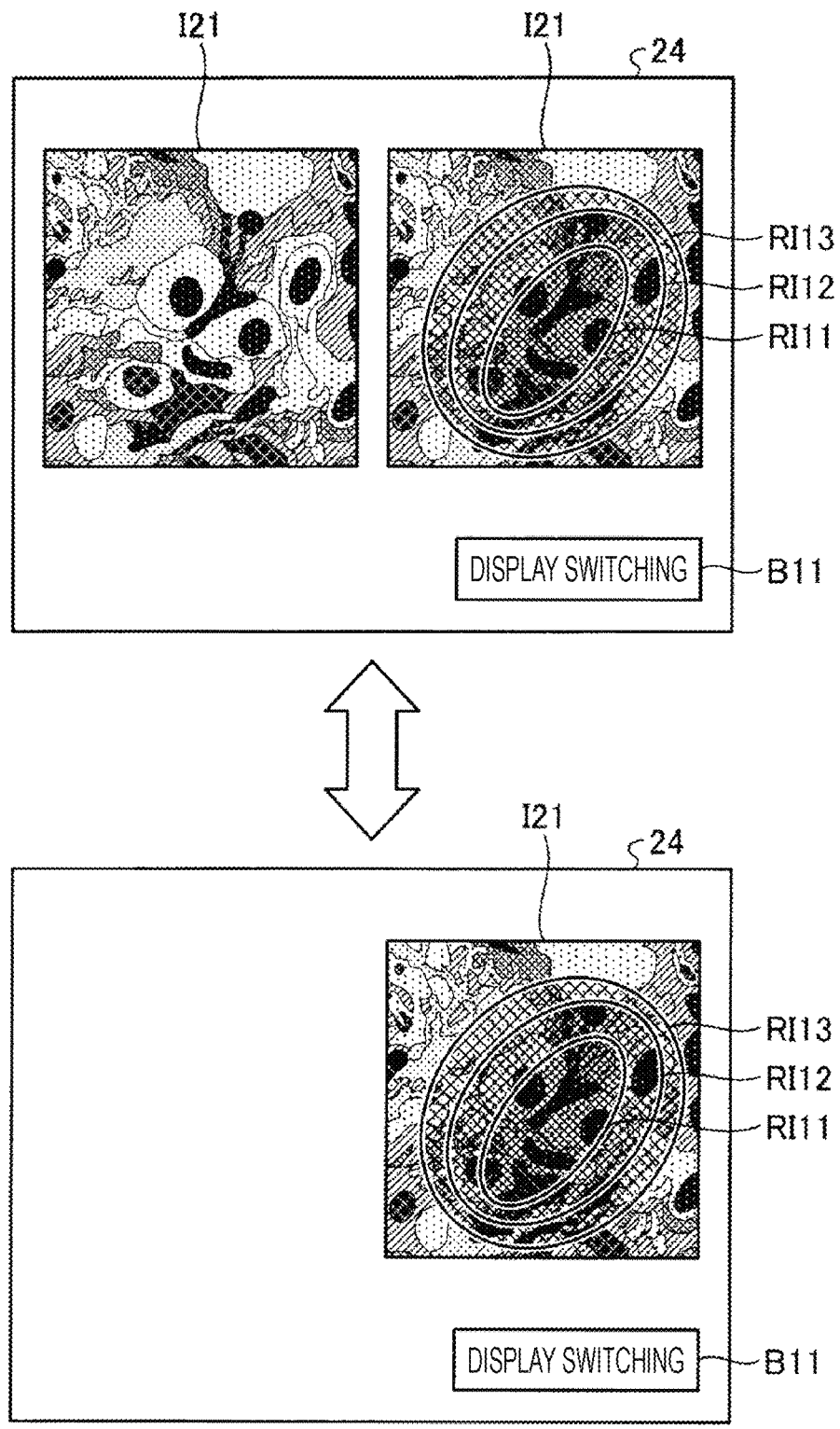
FIG. 14 is a diagram illustrating an example of displaying a pathological image according to a modified example.

Furthermore, as illustrated in FIG. 14, the display control unit 23b displays a display switching button B11. When the display switching button B11 is selected by a viewer, the display control unit 23b may hide the pathological image I21 on which the information indicating the attention region is not superimposed, as illustrated in a lower part of FIG. 14. Then, when the display switching button B11 is selected while the pathological image I21 on which the information indicating the attention region is not superimposed is hidden, the display control unit 23b may display again the pathological image I21 on which the information indicating the attention region is not superimposed as illustrated in an upper part of FIG. 14. This example is not restrictive, and every time the display switching button B11 is selected, the display control unit 23b may switch between and display the pathological image I21 on which the information indicating the attention region is not superimposed and the pathological image I21 on which the information indicating the attention region is superimposed.

[5-2. Display Example (2)]

The example in FIG. 14 shows an example of displaying a plurality of mask images. Alternatively, the display control unit 23b may display a plurality of frame images for each threshold value of the attention score. This point will be described with reference to FIG. 15. In the example illustrated in FIG. 15, the display control unit 23b superimposes and displays, as information indicating an attention region, frame images RI21, RI22, and RI23 of which the inside is not filled on the pathological image I21. Here, it is assumed that the attention score is higher in the order of the frame images RI21, RI22, and RI23. As in the example in FIG. 14, the display control unit 23b may change the saturation, luminance, or transmittance of the frame images RI21, RI22, and RI23 in accordance with the attention scores.

[5-3. Display Example (3)]

Furthermore, the display control unit 23b may automatically display pathological images corresponding to attention regions having a predetermined attention score or more. For example, the display control unit 23b may automatically display each pathological image in descending order of the attention score. Furthermore, for example, the display control unit 23b may switch between and display pathological images, each of which corresponds to one of the attention regions, in the same display area on the display device 24 in accordance with a viewer's operation.

Figure 16:
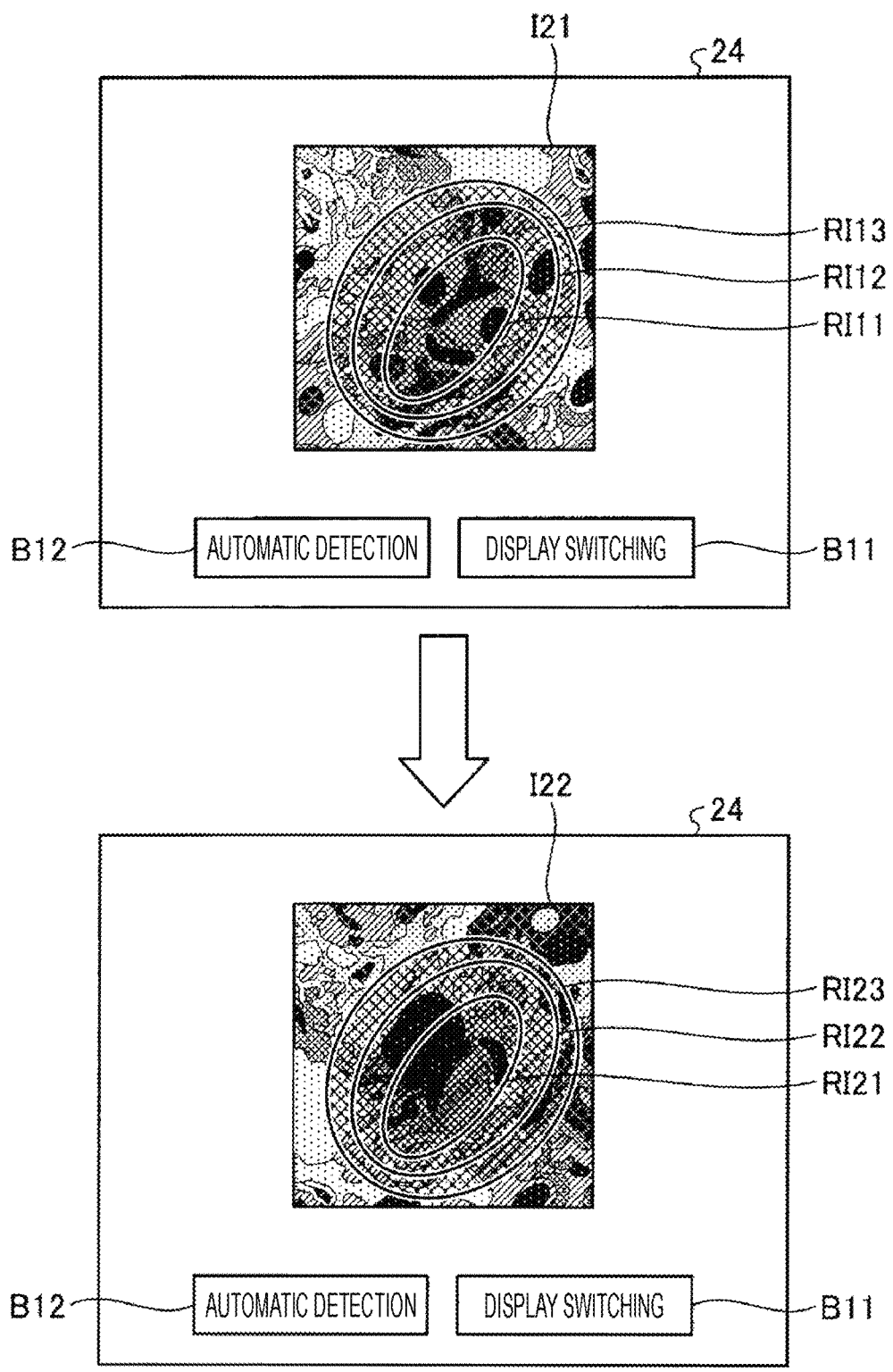
FIG. 16 is a diagram illustrating an example of displaying a pathological image according to a modified example.

This point will be described with reference to FIG. 16. In the example illustrated in an upper part of FIG. 16, as in the example illustrated in FIG. 14, the display control unit 23b superimposes and displays the mask images RI11, RI12, and RI13 on the pathological image I21, and also displays an automatic detection button B12. Here, the display control unit 23b initially displays in an automated manner the pathological image I21 corresponding to a partial region of an entire image, as an image that includes a region with the highest attention score in the entire image. Then, when the automatic detection button B12 is selected by a viewer, the display control unit 23b switches the display to the pathological image I22 that includes a region with the second highest attention score in the entire image as illustrated in a lower part of FIG. 16. Every time the automatic detection button B12 is selected, the display control unit 23b switches the display to a pathological image with the next highest attention score.

[5-4. Display Example (4)]

Figure 15:
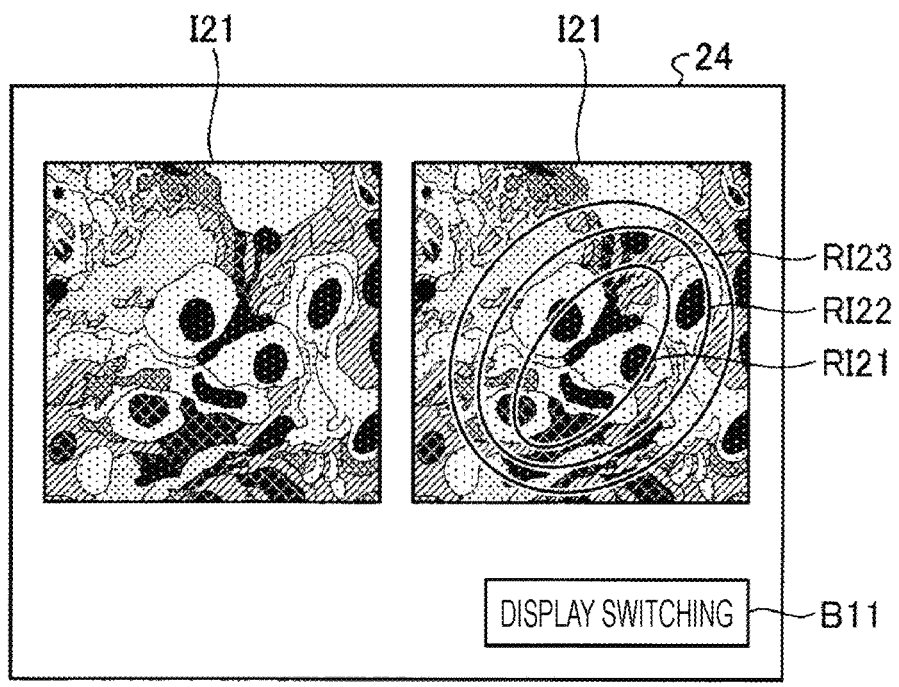
FIG. 15 is a diagram illustrating an example of displaying a pathological image according to a modified example.

Furthermore, as in the examples in FIGS. 14 and 15, in a case where a plurality of frame images or mask images is displayed, the display control unit 23b may change the number of frame images or the number of mask images to be displayed in accordance with a viewer's operation.

Figure 17:
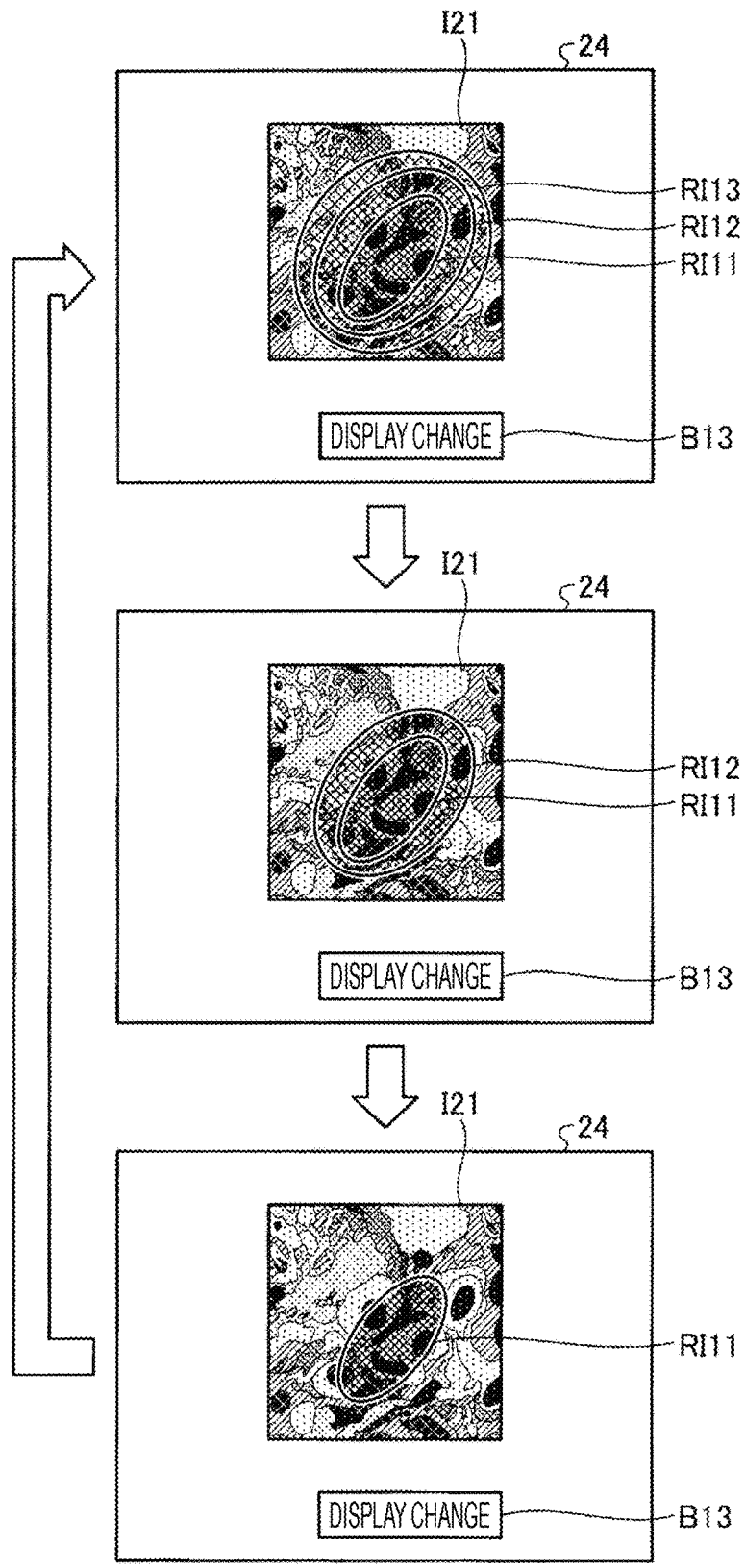
FIG. 17 is a diagram illustrating an example of displaying a pathological image according to a modified example.

This point will be described with reference to FIG. 17. In the example illustrated in an upper part of FIG. 17, as in the example illustrated in FIG. 14, the display control unit 23b superimposes and displays the mask images RI11, RI12, and RI13 on the pathological image I21, and also displays a display change button B13. Here, the display control unit 23b initially displays the three mask images RI11, RI12, and RI13. Then, when the display change button B13 is selected by a viewer, the display control unit 23b hides the mask image RI13 with the lowest attention score among the mask images RI11, RI12, and RI13 as illustrated in a middle part of FIG. 17. Then, when the display change button B13 is selected again, the display control unit 23b displays only the mask image RI11 by hiding the mask image RI12 with the second lowest attention score as illustrated in a lower part of FIG. 17. Then, when the display change button B13 is selected again, the display control unit 23b displays all the mask images RI11, RI12, and RI13 again as illustrated in the upper part of FIG. 17. Note that, when the display change button B13 is selected in a state of the lower part of FIG. 17, the display control unit 23b may hide the mask image RI11 so that all the mask images RI11, RI12, and RI13 are hidden.

[5-5. Display Example (5)]

Furthermore, the display control unit 23b may simultaneously display pieces of information indicating attention regions in a plurality of different regions in a pathological image. This point will be described with reference to FIG. 18. In the example illustrated in FIG. 18, the display control unit 23b displays the pathological image I1 in which the entire observation target A10 is visualized, and also superimposes and displays frame images RI21 to RI25 on the pathological image I1. The frame images RI21 to RI25 indicate attention regions in the pathological image I1, and a viewer can observe in detail the regions corresponding to the frame images RI21 to RI25 while sequentially enlarging the regions.

[5-6. Display Example (6)]

Figure 18:
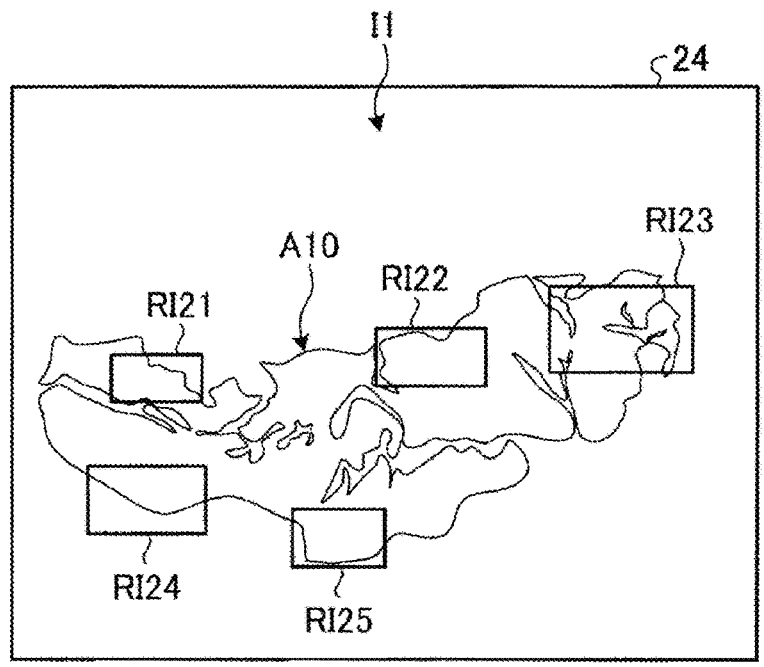
FIG. 18 is a diagram illustrating an example of displaying a pathological image according to a modified example.
Figure 19:
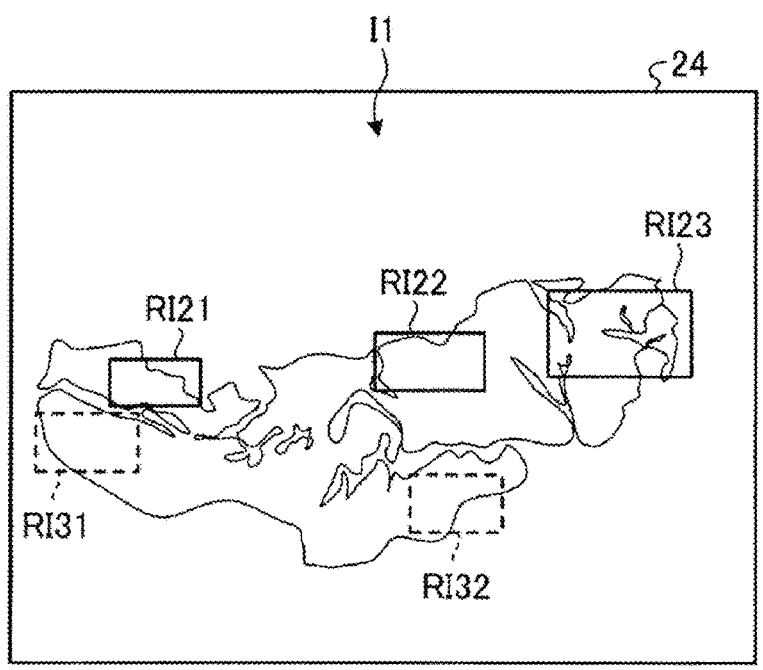
FIG. 19 is a diagram illustrating an example of displaying a pathological image according to a modified example.

Furthermore, the display control unit 23b may display a frame image or a mask image indicating a non-attention region in the example in FIG. 18. For example, the display control unit 23b displays a frame image or the like indicating a non-attention region in a region where the attention score output by the learning model 121 is lower than a predetermined threshold value TH3. This point will be described with reference to FIG. 19. In the example illustrated in FIG. 19, the display control unit 23b displays the pathological image I1 in which the entire observation target A10 is visualized, displays the frame images RI21 to RI23 indicating attention regions, and also displays frame images R131 and R132 indicating non-attention regions. The frame images R131 and R132 indicate that the regions have not been viewed with attention in the past. This means that the regions corresponding to the frame images R131 and R132 require only simple observation, and allows for efficient pathological diagnosis. Note that the display control device 23 can specify non-attention regions by acquiring, from the derivation device 100, the attention score corresponding to each region in the pathological image I1 as diagnosis support information.

[5-7. Display Example (7)]

Figure 20:
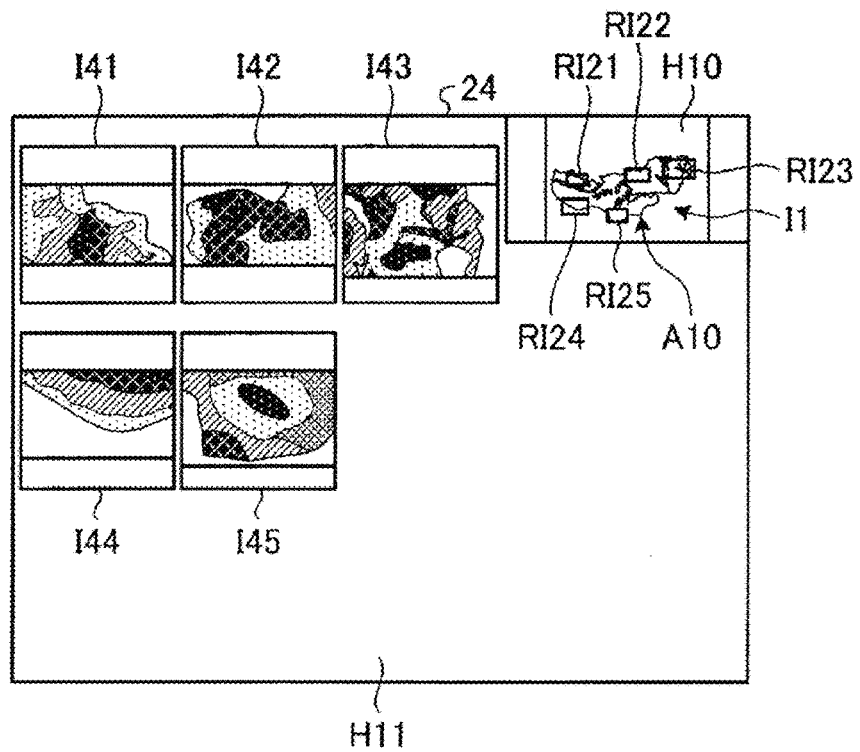
FIG. 20 is a diagram illustrating an example of displaying a pathological image according to a modified example.

Furthermore, the display control unit 23b may display pathological images corresponding to a plurality of attention regions side by side. This point will be described with reference to FIG. 20. As illustrated in FIG. 20, the display control unit 23b displays a screen that includes the entire display region H10 and the enlarged display region H11. In the example in FIG. 20, the display control unit 23b displays, in the entire display region H10, the pathological image I1 and the frame images RI21 to RI25 illustrated in FIG. 18. Then, in the enlarged display region H11, the display control unit 23b displays pathological images corresponding to the frame images RI21 to RI25 side by side. In the example in FIG. 20, the display control unit 23b displays a pathological image I41 corresponding to the frame image RI21, a pathological image I42 corresponding to the frame image RI22, a pathological image I43 corresponding to the frame image RI23, a pathological image I44 corresponding to the frame image RI24, and a pathological image I45 corresponding to the frame image RI25. At this time, the display control unit 23b may display the pathological images I41 to I45 in descending order of the attention score.

[5-8. Display Example (8)]

Figure 21:
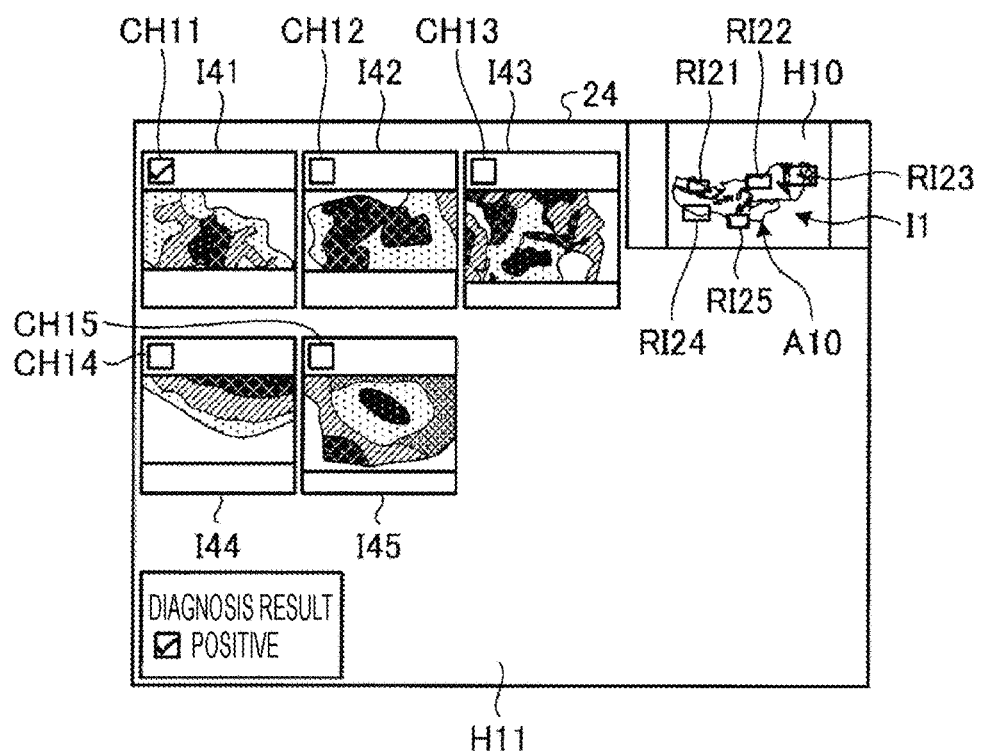
FIG. 21 is a diagram illustrating an example of displaying a pathological image according to a modified example.

Furthermore, the display control unit 23b may display, in a selectable manner, a plurality of the pathological images corresponding to attention regions in the example in FIG. 20. Then, the display control unit 23b may save a selected pathological image as diagnosis result information to a storage unit of the server 22. This point will be described with reference to FIG. 21. As illustrated in FIG. 21, as in the example in FIG. 20, the display control unit 23b superimposes and displays the frame images RI21 to RI25 on the pathological image I1 in the entire display region H10. Furthermore, in the enlarged display region H11, the display control unit 23b displays, in a selectable manner, the pathological images I41 to I45 side by side. Specifically, the display control unit 23b displays check boxes CH11 to CH15 for selecting each of the pathological images I41 to I45. Then, in a case where a save button (not illustrated) is pressed with these check boxes selected, the display control unit 23b saves a selected pathological image to the storage unit of the server 22 or the medical information system 30.

[5-9. Display Example (9)]

Furthermore, for a developer who generates a learning model, the display control unit 23b may display a result of learning in which a learning parameter has been changed. Furthermore, the display control unit 23b may display learning results corresponding to different learning parameters side by side in a comparable manner. Note that examples of the learning parameters include a threshold value TH4 that causes a value equal to or less than a predetermined attention index value in a heat map image to be 0, a batch size or an input size of learning, and a network configuration of deep learning.

Figure 22:
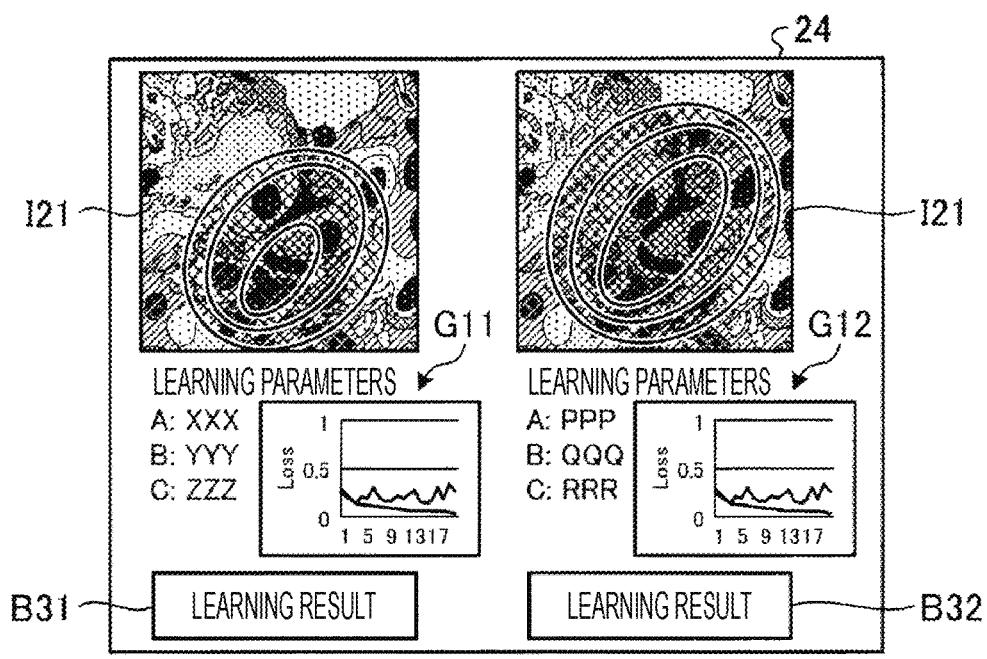
FIG. 22 is a diagram illustrating an example of displaying a pathological image according to a modified example.

This point will be described with reference to FIG. 22. In the example in FIG. 22, the display control unit 23b displays two learning results side by side. Specifically, the display control unit 23b displays, on the left side of the screen, a result of learning in which a learning parameter A is "XXX", a learning parameter B is "YYY", and a learning parameter C is "ZZZ". Furthermore, the display control unit 23b displays, on the right side of the screen, a result of learning in which the learning parameters A, B, and C are "PPP", "QQQ", and "RRR". For example, the display control unit 23b superimposes and displays, as the learning results, information indicating attention regions (mask images in the example in FIG. 22) on the pathological image I21. Furthermore, as illustrated in FIG. 22, the display control unit 23b displays graphs G11 and G12 indicating a relationship between the number of times of learning and an output of a loss function in machine learning. In the graphs G11 and G12 illustrated in FIG. 22, a vertical axis represents the output of the loss function, and a horizontal axis represents the number of times of learning. The number of times of learning corresponds to, for example, the number of times back propagation is performed (that is, the number of times a weight is updated) when a neural network is learned. Note that learning is performed as needed, and the display control unit 23b displays information regarding the latest learning result when a learning result button B31 or B32 is selected.

[5-10. Display Example (10)]

Furthermore, in the above description, frame images and mask images have been described as examples of diagnosis support information to be superimposed and displayed on a pathological image. Alternatively, as an example of the diagnosis support information, the display control unit 23b may superimpose and display an arrow image pointing to the attention region on the pathological image, or may display text information, which is a description regarding the attention region.

[5-11. Pathological Images with Different Imaging Conditions]

Furthermore, as described in [2-1. Pathological image], tile images, which are pathological images, may be generated for each imaging condition such as the focal length or the staining condition. In a case where tile images are generated for each imaging condition, the display control unit 23b displays, for example, a pathological image corresponding to a specific imaging condition (hereinafter referred to as a specific pathological image) in the examples described with reference to FIGS. 11 and 14 to 22. At this time, the display control unit 23b may display, side by side, the specific pathological image and another pathological image that corresponds to an imaging condition different from the specific imaging condition and is in the same region as the specific pathological image. In this case, the display control unit 23b displays information indicating an attention region (a mask image, a frame image, or the like) at a position, in the other pathological image, corresponding to an attention region of the specific pathological image. Note that the specific imaging condition may be designated by a viewer. Furthermore, in a case where a viewer has designated a plurality of imaging conditions, the display control unit 23b may display, side by side, pathological images of the same region, each of the pathological images corresponding to one of the imaging conditions.

[5-12. Diagnosis Prediction Result]

Furthermore, in the examples illustrated in FIGS. 11 and 14 to 22, the display control unit 23b may display, together with information indicating an attention region (a mask image, a frame image, or the like), a diagnosis result and prediction information. As described above, it can be said that an attention score derived with the use of the learning model 121 indicates the probability that a lesion area exists. That is, it can be said that an attention score corresponding to each region in the second pathological image indicates the probability that a lesion exists in each region. The display control unit 23b may display information regarding the probability of existence of a lesion determined from such an attention score. For example, in the examples illustrated in FIGS. 11 and 14 to 22, the display control unit 23b may superimpose and display, together with information indicating an attention region (a mask image, a frame image, or the like), information regarding the probability of existence of a lesion.

Furthermore, information displayed by the display control unit 23b is not limited to the information described above, and the display control unit 23b may display additional information as appropriate. For example, the display control unit 23b may display a resolution of a pathological image. Furthermore, the display control unit 23b may display a recommended size or the like for displaying an object of observation on the basis of viewing history information. Furthermore, the display control unit 23b may display past pathological images of the same patient side by side. Furthermore, the display control unit 23b may display a pathological image of another patient similar to a pathological image to be displayed.

6. Modified Examples 2

Hereinafter, modified examples of the learning processing will be described.

[6-1. Learning Processing (1)]

In the above embodiment, an example has been described in which the learning unit 133 performs learning by using viewing history information acquired from the server 12. Alternatively, the learning unit 133 may acquire a pathological image stored in the medical information system 30 as the viewing history information. Specifically, as described with reference to FIGS. 9A to 9C, a diagnostic information storage unit of the medical information system 30 stores a pathological image saved by a pathologist at the time of diagnosis. A pathologist often enlarges and saves a region of a pathological image in which a lesion area has been found. That is, the pathological image stored in the diagnostic information storage unit is an image of a partial region of an entire image, and often corresponds to a region where a lesion area has been found or a region where there is a high possibility that a lesion area is contained. Thus, the learning unit 133 performs learning assuming that the pathological image stored in the medical information system 30 contains a region to which attention is to be paid. For example, in a case where a heat map image is generated from a first pathological image stored in the server 12, the learning unit 133 adds a predetermined value to an attention index value of a region, in the first pathological image, corresponding to the pathological image acquired from the medical information system 30. This allows the learning unit 133 to learn in consideration of not only a viewing operation by a pathologist but also a pathological image that has actually attracted attention and been saved by a pathologist, and thus, it is possible to generate the learning model 121 that is highly accurate.

[6-2. Learning Processing (2)]

Furthermore, in the above embodiment, the learning unit 133 may learn by using only an entire image of a first pathological image. Then, the learning unit 133 may use position information of a region viewed with attention in the entire image as viewing history information used for the learning processing. This allows the learning unit 133 to generate the learning model 121 capable of estimating a region to which particular attention is to be paid in the entire image corresponding to an entire observation target.

[6-3. Learning Processing (3)]

Furthermore, the learning unit 133 may perform learning with weighting based on information regarding an observation target (here, a first affected tissue). For example, the learning unit 133 can use, as information regarding the observation target, information regarding a patient from which the first affected tissue has been collected (gender, age, medical history, and the like), site information regarding the first affected tissue (large intestine, lung, or the like), a reagent used to stain the first affected tissue, information regarding an organization that has stained the first affected tissue, a type and a degree of progression of a lesion site in the observation target, and the like.

For example, the learning unit 133 may perform learning in which the older the patient is, the more weighted the first pathological image corresponding to the patient is. Furthermore, for example, the learning unit 133 may perform learning in which the more reliable the organization that has stained the first affected tissue is, the more weighted the first pathological image corresponding to the first affected tissue stained by the organization is.

Furthermore, the learning unit 133 may generate a learning model for each piece of information regarding the first affected tissue by performing learning separately for each piece of the information regarding the first affected tissue. For example, the learning unit 133 generates a learning model for males on the basis of first pathological images of only males, and generates a learning model for females on the basis of first pathological images of only females. In this case, the derivation unit 134 performs derivation processing by using a learning model for the gender that coincides with the gender of a patient corresponding to a second pathological image, which is an object of prediction. In other examples as well, the learning unit 133 may generate a learning model for the large intestine and a learning model for the lung, or may generate a learning model for a staining organization A and a learning model for a staining organization B. Furthermore, for example, in a case of generating a learning model for the large intestine, the learning unit 133 may perform learning in which first pathological images of males, who have a high incidence rate of the large intestine, are weighted more than first pathological images of females. Furthermore, for example, in a case of generating a learning model for breast cancer, the learning unit 133 may perform learning in which first pathological images of females, who have a high incidence rate of breast cancer, are weighted more than first pathological images of males.

Note that, in a case where the learning unit 133 has generated a learning model for each piece of information regarding the first affected tissue, the derivation unit 134 may use each learning model to derive diagnosis support information. For example, the derivation unit 134 may use the learning model for the staining organization A to derive diagnosis support information X1, and use the learning model for the staining organization B to derive diagnosis support information X2. Then, the display control unit 23b may superimpose and display, on the same pathological image, both information indicating an attention region (a mask image or the like) based on the diagnosis support information X1 and information indicating an attention region based on the diagnosis support information X2. At this time, the display control unit 23b may change the display mode (saturation, luminance, transmittance, or the like) of the information indicating the attention region in accordance with the degree of reliability of the diagnosis support information. For example, in a case where the staining organization B has a higher degree of reliability than the staining organization A, the display control unit 23b determines that the diagnosis support information X2 has a higher degree of reliability than the diagnosis support information X1. Furthermore, in the example in FIG. 16, the display control unit 23b may switch the display of a pathological image in accordance with the degree of reliability of the diagnosis support information. For example, the display control unit 23b displays pathological images corresponding to regions specified by pieces of diagnosis support information in descending order of the degree of reliability of the diagnosis support information. Furthermore, in the example in FIG. 20, the display control unit 23b may display pathological images side by side in accordance with the degree of reliability of the diagnosis support information. For example, the display control unit 23b displays, side by side, pathological images corresponding to regions specified by pieces of diagnosis support information in descending order of the degree of reliability of the diagnosis support information.

Furthermore, the learning unit 133 generates a learning model for each type of the lesion site (tissue types illustrated in FIGS. 9A to 9C) in the observation target. In this case, by using each learning model for a second pathological image, the derivation unit 134 can derive an attention score corresponding to each region in the second pathological image, that is, the probability that a lesion area exists for each type of the lesion site. Based on such an attention score, the display control unit 23b may display, together with information indicating an attention region (a mask image, a frame image, or the like), the probability that a lesion area exists for each type of the lesion site. In a similar manner, in a case where the learning unit 133 has generated a learning model for each degree of progression (grades illustrated in FIGS. 9A to 9C) of the observation target, the display control unit 23b may display information regarding the grade of the lesion area.

[6-4. Learning Processing (4)]

Furthermore, the learning unit 133 may perform learning with weighting based on information regarding imaging of the first pathological image. For example, the learning unit 133 can use, as information regarding imaging of the first pathological image, information regarding a device that has captured the first pathological image, an organization that has captured the first pathological image, and the like.

For example, the learning unit 133 may perform learning in which the higher the accuracy of the device that has captured the first pathological image is, the more weighted the first pathological image captured by the device is. Furthermore, for example, the learning unit 133 may perform learning in which the more reliable the organization that has captured the first pathological image is, the more weighted the first pathological image captured by the organization is. Furthermore, the learning unit 133 may generate a learning model for each piece of information regarding imaging of the first pathological image by performing learning separately for each piece of the information regarding imaging of the first pathological image. Furthermore, the display control unit 23b may display a plurality of pieces of diagnosis support information derived with the use of each learning model. Furthermore, the display control unit 23b may change the display mode of information indicating an attention region in accordance with the degree of reliability of the diagnosis support information determined by the degree of reliability of the imaging device or the imaging organization.

[6-5. Learning Processing (5)]

Furthermore, the learning unit 133 may perform learning with weighting based on information regarding display of the first pathological image. For example, the learning unit 133 can use information regarding a device used to display the first pathological image, a program used to display the first pathological image, a viewing time of a region where the first pathological image is displayed, the number of times the region where the first pathological image is displayed, or the like.

For example, the learning unit 133 may perform learning in which the higher the accuracy of a display device used to display the first pathological image is, the more weighted the first pathological image displayed by the display device for diagnosis is. Furthermore, for example, the learning unit 133 may perform learning in which the higher the accuracy of the program used to display the first pathological image is, the more weighted the first pathological image displayed by the program for diagnosis is. Note that, as for the viewing time and the number of times of display, as described above, the learning unit 133 performs learning on the basis of a heat map image in which an attention index value is reflected as a weight in accordance with the viewing time or the number of times of display. Furthermore, the learning unit 133 may generate a learning model for each piece of information regarding the display of the first pathological image by performing learning separately for each piece of the information regarding the display of the first pathological image. Furthermore, the display control unit 23b may display a plurality of pieces of diagnosis support information derived with the use of each learning model. Furthermore, the display control unit 23b may change the display mode of information indicating an attention region in accordance with the degree of reliability of the diagnosis support information determined by the degree of reliability of the display device or the display program.

[6-6. Learning Processing (6)]

Furthermore, the learning unit 133 may perform learning with weighting based on information regarding a user (that is, a viewer of a first pathological image) corresponding to viewing history information. For example, the learning unit 133 can use, as the information regarding the user corresponding to the viewing history information, information for specifying a diagnostician who has diagnosed the first pathological image, information indicating an ability rank of the diagnostician, or the like.

For example, the learning unit 133 may perform learning in which the higher the diagnostic level or the ability rank of the diagnostician who has diagnosed the first pathological image is, the more weighted the first pathological image viewed by the diagnostician is. The diagnostic level and the ability rank of the diagnostician are determined on the basis of years of experience, the number of cases experienced, and the like. Furthermore, the learning unit 133 may generate a learning model for each piece of information regarding the user corresponding to the viewing history information by performing learning separately for each piece of the information regarding the user corresponding to the viewing history information. Furthermore, the display control unit 23b may display a plurality of pieces of diagnosis support information derived with the use of each learning model. Furthermore, the display control unit 23b may change the display mode of information indicating an attention region in accordance with the degree of reliability of the diagnosis support information determined by the degree of reliability of the diagnostic level or the ability rank of the diagnostician.

[6-7. Learning Processing (7)]

Furthermore, the above embodiment shows an example in which a heat map image is used for learning, but the learning unit 133 may perform learning without using a heat map image. For example, the learning unit 133 may perform learning in which the time of viewing by a pathologist, the number of times of viewing, the magnification ratio, and the like for each region in a first pathological image are used as explanatory variables, and an attention score (e.g., 0 to 1) indicating the degree of attention of the pathologist for each region in the pathological image is used as an objective variable. At this time, the learning unit 133 performs learning such that a region with a longer viewing time has a higher attention score, a region with a larger number of times of viewing has a higher attention score, a region that has been enlarged and viewed more has a higher attention score, and a region with a higher magnification ratio has a higher attention score.

[6-8. Learning Processing (8)]

Furthermore, the viewing history storage unit 12a illustrated in FIG. 8 may store information regarding a line-of-sight of a viewer viewing a first pathological image. For example, the viewing history storage unit 12a stores, as line-of-sight information, position information of a region in the first pathological image viewed by the viewer for a predetermined time or more, or a region in the first pathological image viewed a predetermined number of times or more. Such line-of-sight information can be acquired by a technology such as eye tracking. Then, the learning unit 133 may perform learning in consideration of the line-of-sight information stored in the viewing history storage unit 12a. For example, the learning unit 133 performs learning after an attention index value based on the line-of-sight information has been reflected in the heat map image described above.

Second Embodiment

In the first embodiment described above, an example of deriving diagnosis support information by using a learning model has been described. In a second embodiment, an example of deriving diagnosis support information without using a learning model will be described.

Figure 23:
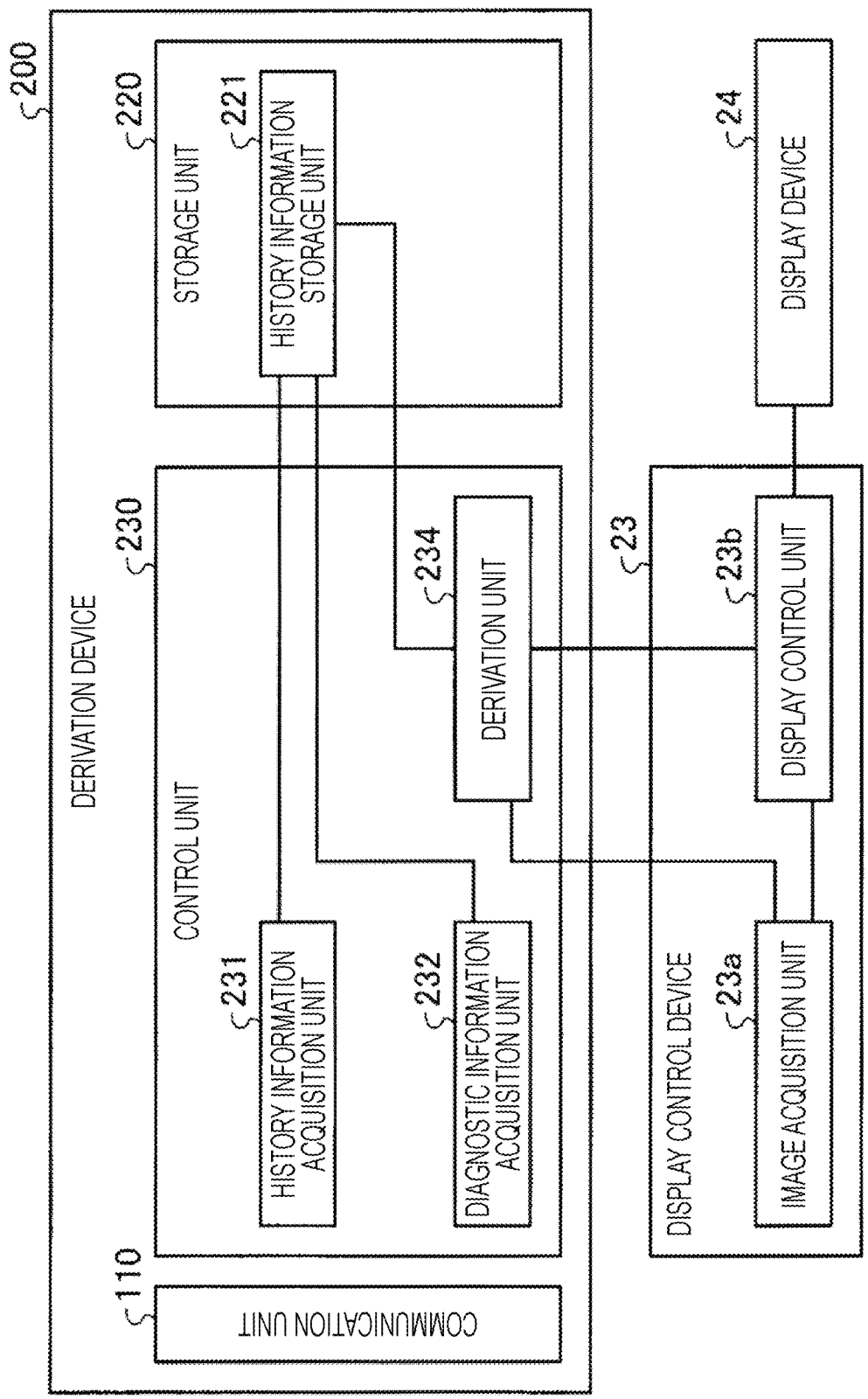
FIG. 23 is a diagram illustrating an example of a derivation device and a display control device according to a second embodiment.

FIG. 23 is a diagram illustrating an example of a derivation device 200 and a display control device 23 according to the second embodiment. As illustrated in FIG. 23, the derivation device 200 includes a communication unit 110, a storage unit 220, and a control unit 230.

The storage unit 220 is constituted by, for example, a semiconductor memory element such as a RAM or a flash memory, or a storage device such as a hard disk or an optical disk. The storage unit 220 includes a history information storage unit 221.

The control unit 230 is implemented by, for example, a CPU or an MPU executing a diagnosis support program stored in the derivation device 200 by using a RAM or the like as a working area. Furthermore, the control unit 230 may be executed by an integrated circuit such as an ASIC or an FPGA. As illustrated in FIG. 23, the control unit 230 includes a history information acquisition unit 231, a diagnostic information acquisition unit 232, and a derivation unit 234.

The history information acquisition unit 231 acquires, from a server 12 of a pathology system 10, a first pathological image and viewing history information regarding viewing of the first pathological image, and stores the acquired first pathological image and viewing history information in the history information storage unit 221.

The diagnostic information acquisition unit 232 acquires, from a medical information system 30, diagnostic information for a first affected tissue corresponding to the first pathological image, and stores the acquired diagnostic information in the history information storage unit 221.

In a case where a second pathological image has been received from the display control device 23, the derivation unit 234 refers to the history information storage unit 221 to derive diagnosis support information on the basis of the viewing history information regarding first pathological images having a similarity to the second pathological image higher than a predetermined threshold value TH4. Specifically, the derivation unit 234 specifies, from among first pathological images stored in the history information storage unit 221, a first pathological image in which a similarity in feature amount to the second pathological image is higher than the threshold value TH4 and a positive diagnosis result has been obtained. Then, on the basis of viewing history information corresponding to the specified first pathological image, the derivation unit 234 derives, as diagnosis support information, position information and the like of a region in the second pathological image similar to an attention region of the first pathological image.

Note that the derivation unit 234 may derive the diagnosis support information on the basis of viewing history information regarding a first pathological image having a degree of correlation with the second pathological image higher than a predetermined threshold value TH5. The degree of correlation herein corresponds to coincidence of attributes (gender, age, and the like) of patients, coincidence of affected tissues, and the like.

In this manner, the derivation device 200 according to the second embodiment derives diagnosis support information without using a learning model. Note that the display processing by the display control device 23 described in the first embodiment can be applied to the second embodiment.

Other Embodiments

The processing according to each embodiment described above may be performed in a variety of different modes other than each embodiment described above.

[Display Device]

The above embodiments show an example in which information indicating an attention region such as a mask image is superimposed and displayed on a pathological image displayed on the stationary display device 24. Alternatively, the information indicating the attention region may be displayed on a wearing device (a head mounted display or the like) worn by a viewer viewing the pathological image displayed on the display device 24. Thus, the information indicating the attention region displayed on the wearing device may be superimposed on the pathological image displayed on the display device 24. Furthermore, the information indicating the attention region may be displayed on a transparent display mounted so as to cover the front surface of the display device 24. Thus, the information indicating the attention region displayed on the transparent display may be superimposed on the pathological image displayed on the display device 24.

[Imaging Device]

Furthermore, in the above embodiments, a microscope has been described as an example of a device for imaging an observation target, but this is not restrictive. For example, the device for imaging the observation target may be a medical image acquisition device such as an endoscope for imaging the inside of a body of a patient, computed tomography (CT), or magnetic resonance image (MRI). In this case, medical images such as two-dimensional still images or moving images generated by the endoscope, three-dimensional images generated by the CT and the MRI, and the like are saved to the server 12 and the server 22. Furthermore, the server 12 and the server 22 may store, in association with these images, information related to the image such as an imaging condition and a diagnosis result for the image.

[Server]

Furthermore, the server 12 and the server 22 may store, in association with a pathological image generated by the microscope, another pathological image captured by another medical image acquisition device such as an endoscope, CT, or MRI. In this case, in addition to the pathological image generated by the microscope, the display control unit 23*b* may display another pathological image captured by another imaging device side by side for reference.

[Pathological Image]

Pathological images saved on the server 12 and the server 22 include pathological images having a lower resolution. That is, although there is viewing history information, the resolution of the pathological image corresponding to the viewing history information may not be sufficient for appropriate learning. Here, in a case where a glass slide containing an observation target has been saved, an image of the glass slide may be re-captured with a high-resolution microscope so that a high-resolution pathological image is newly generated. Thus, in a case where a first pathological image for learning does not have a resolution sufficient for appropriate learning and there is a re-captured pathological image, the derivation device 100 may perform the learning described above in which viewing history information of the first pathological image is associated with the re-captured pathological image. At this time, the derivation device 100 performs processing such that the first pathological image is aligned with the re-captured pathological image, and an attention region indicated by the viewing history information of the first pathological image corresponds to a region of the re-captured pathological image.

[Hardware Configuration]

Figure 24:
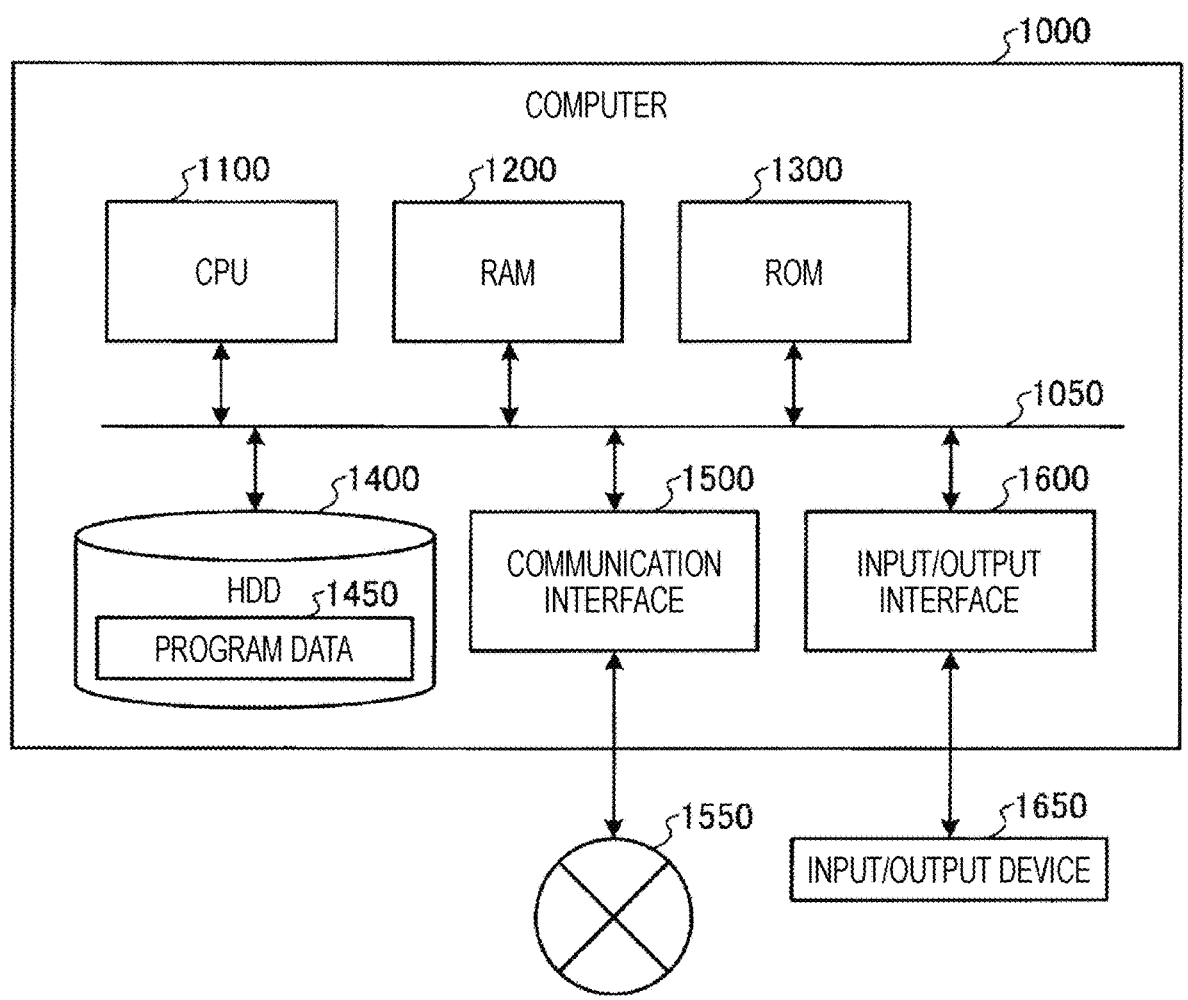
FIG. 24 is a hardware configuration diagram illustrating an example of a computer that implements functions of the derivation device.

The information devices such as the derivation devices 100 and 200 and the display control device 23 according to each embodiment described above are implemented by a computer 1000 having a configuration as illustrated in FIG. 24, for example. The derivation device 100 according to the first embodiment will be described below as an example. FIG. 24 is a hardware configuration diagram illustrating an example of the computer 1000 that implements functions of the derivation device 100. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates on the basis of a program stored in the ROM 1300 or the HDD 1400, and controls each unit. For example, the CPU 1100 decompresses, on the RAM 1200, the program stored in the ROM 1300 or the HDD 1400, and executes processing corresponding to various programs.

The ROM 1300 stores a boot program such as a basic input output system (BIOS) executed by the CPU 1100 when the computer 1000 is activated, a program depending on hardware of the computer 1000, and the like.

The HDD 1400 is a computer-readable recording medium that non-temporarily records a program to be executed by the CPU 1100, data to be used by the program, and the like. Specifically, the HDD 1400 is a recording medium that records a response generation program according to the present disclosure as an example of program data 1450.

The communication interface 1500 is an interface for the computer 1000 to connect to an external network 1550 (e.g., the Internet). For example, the CPU 1100 receives data from another device or transmits data generated by the CPU 1100 to another device via the communication interface 1500.

The input/output interface 1600 is an interface for connecting an input/output device 1650 and the computer 1000. For example, the CPU 1100 receives data from an input device such as a keyboard and a mouse via the input/output interface 1600. Furthermore, the CPU 1100 transmits data to an output device such as a display, a speaker, or a printer via the input/output interface 1600. Furthermore, the input/output interface 1600 may function as a media interface that reads a program or the like recorded on a predetermined computer-readable recording medium (medium). The medium is, for example, an optical recording medium such as a digital versatile disc (DVD) or a phase change rewritable disk (PD), a magneto-optical recording medium such as a magneto-optical disk (MO), a tape medium, a magnetic recording medium, or a semiconductor memory.

For example, in a case where the computer 1000 functions as the derivation device 100 according to the first embodiment, the CPU 1100 of the computer 1000 executes the diagnosis support program loaded on the RAM 1200 to implement the functions of the history information acquisition unit 131, the diagnostic information acquisition unit 132, the learning unit 133, the derivation unit 134, and the like. Furthermore, the HDD 1400 stores the diagnosis support program according to the present disclosure and data in the storage unit 120. Furthermore, for example, in a case where the computer 1000 functions as the display control device 23 according to the first embodiment, the CPU 1100 of the computer 1000 executes the display control program loaded on the RAM 1200 to implement the functions of the image acquisition unit 23a, the display control unit 23b, and the like. Furthermore, the HDD 1400 stores the display control program according to the present disclosure. Note that the CPU 1100 reads the program data 1450 from the HDD 1400 and executes the program data. As another example, the diagnosis support program and the display control program may be acquired from another device via the external network 1550.

[Others]

Among the pieces of processing described in each embodiment described above, all or a part of the processing described as being automatically performed can be manually performed. Alternatively, all or a part of the processing described as being manually performed can be automatically performed by a known method. In addition, the processing procedures, specific names, and information including various types of data and parameters described so far or illustrated in the drawings can be optionally changed unless otherwise specified. For example, the various types of information illustrated in each drawing are not limited to the illustrated information.

Furthermore, each component of each device illustrated in the drawings is functionally conceptual, and is not necessarily physically configured as illustrated in the drawings. That is, a specific mode of distribution and integration of each device is not limited to the illustrated mode, and all or a part thereof can be functionally or physically distributed or integrated in an optional unit in accordance with various loads, usage conditions, and the like.

Furthermore, the embodiments and modified examples described above can be combined as appropriate as long as a contradiction does not occur in the contents of the processing.

(Effects)

As described above, the derivation device 100 (or 200) causes a computer to execute a derivation procedure of deriving diagnosis support information for supporting diagnosis of a second pathological image corresponding to a second affected tissue to be diagnosed, on the basis of a first pathological image corresponding to a first affected tissue, history information regarding a history of viewing the first pathological image (the viewing history information described above), and diagnostic information for the first affected tissue corresponding to the first pathological image. Furthermore, the diagnosis support system 1 includes the microscope 11 (or 21) and the derivation device 100 (or 200) that derives diagnosis support information, which is information for supporting diagnosis. Note that the processing by the derivation device 100 may be performed by software used for processing of a pathological image corresponding to an object to be imaged by the microscope 11 (or 21). Note that, in the following description of effects, the derivation device 100 can be replaced with the derivation device 200.

Thus, according to the above embodiments, the diagnosis accuracy can be improved on the basis of the diagnosis support information.

Furthermore, the derivation device 100 derives information regarding viewing as the diagnosis support information.

Thus, according to the above embodiments, the diagnosis accuracy at the time of viewing can be improved.

Furthermore, the derivation device 100 derives the diagnosis support information by using the viewing history information corresponding to the diagnostic information with a positive diagnosis result.

Thus, according to the above embodiments, the diagnosis support information is derived in consideration of the viewing history information in a positive case, and this improves the positive diagnosis accuracy.

Furthermore, the viewing history information includes information regarding an image of a partial region of the first pathological image saved at the time of diagnosis of the first pathological image. Furthermore, the derivation device 100 acquires an image of a partial region of the first pathological image from a medical information system in which patient information corresponding to the first pathological image is registered.

Thus, according to the above embodiments, the diagnosis support information is derived in consideration of a pathological image that has actually attracted attention and been saved by a pathologist, and this further improves the diagnosis accuracy.

Furthermore, the first pathological image is an entire image obtained by imaging the entire first affected tissue. Furthermore, the viewing history information is position information indicating a position where the first pathological image has been viewed.

Thus, according to the above embodiments, the diagnosis support information of the entire first affected tissue can be derived, and this makes it possible to support diagnosis of the entire first affected tissue without omission.

Furthermore, the viewing history information is position information indicating a position where the first pathological image has been viewed, and information indicating a time or the number of times the first pathological image has been viewed.

Thus, according to the above embodiments, the diagnosis support information is derived on the basis of a region that the pathologist has viewed with attention, and this further improves the diagnosis accuracy.

Furthermore, the first pathological image is an image constituted by a partial image corresponding to each region of the first affected tissue. Furthermore, the viewing history information is partial image information indicating a viewed partial image among the partial images corresponding to the regions. Furthermore, the partial image information is information indicating a position of the partial image or specifying the partial image.

Thus, according to the above embodiments, the diagnosis accuracy can be improved even in a system in which a pathological image is constituted by partial images.

Furthermore, the derivation device 100 derives the diagnosis support information on the basis of an attention region of the second pathological image estimated from the viewing history information.

Thus, according to the above embodiments, it is possible to provide a region to which attention is to be paid in the second pathological image to be diagnosed, and this facilitates a diagnosis work and reduces the variation in diagnosis.

Furthermore, the derivation device 100 derives the diagnosis support information on the basis of the viewing history information, assuming that a region with a larger display magnification is an attention region with a higher degree of attention, a region with a longer viewing time is an attention region with a higher degree of attention, or a region with a larger number of times of viewing is an attention region with a higher degree of attention.

Thus, according to the above embodiments, a region to which attention is to be paid can be specified with high accuracy, and this further improves the diagnosis accuracy.

Furthermore, the diagnostic information is information regarding whether a lesion site has been found, a type of the lesion site, or a degree of progression of the lesion site. Furthermore, the diagnostic information is acquired from the medical information system in which patient information corresponding to the first pathological image is registered.

Thus, according to the above embodiments, it is possible to derive the diagnosis support information in accordance with whether a lesion site has been found, a type of the lesion site, or a degree of progression of the lesion site.

Furthermore, the derivation device 100 learns an association among the first pathological image, the viewing history information, and the diagnostic information. Furthermore, the derivation device 100 derives the diagnosis support information by using a learning result.

Thus, according to the above embodiments, the viewing history information is used, so that the diagnosis support information can be accurately derived in the framework for supervised learning that does not require detailed annotation data such as weakly supervised learning.

Furthermore, the derivation device 100 performs learning with weighting based on information regarding the first affected tissue, or performs learning separately for each piece of the information regarding the first affected tissue. Furthermore, the information regarding the first affected tissue is information regarding a patient from which the first affected tissue has been collected, site information regarding the first affected tissue, a reagent used to stain the first affected tissue, or information regarding an organization that has stained the first affected tissue.

Thus, according to the above embodiments, it is possible to derive the diagnosis support information with higher accuracy by using the information regarding the first affected tissue.

Furthermore, the derivation device 100 performs learning with weighting based on information regarding imaging of the first pathological image, or performs learning separately for each piece of the information regarding imaging of the first pathological image. Furthermore, the information regarding imaging of the first pathological image is information regarding a device that has captured the first pathological image or an organization that has captured the first pathological image.

Thus, according to the above embodiments, the diagnosis support information can be derived with higher accuracy by using the information regarding imaging of the first pathological image.

Furthermore, the derivation device 100 performs learning with weighting based on information regarding display of the first pathological image, or performs learning separately for each piece of the information regarding display of the first pathological image. Furthermore, the information regarding the display of the first pathological image is information regarding a device used to display the first pathological image, a program used to display the first pathological image, a viewing time of a region where the first pathological image is displayed, or the number of times the region where the first pathological image is displayed.

Thus, according to the above embodiments, the diagnosis support information can be derived with higher accuracy by using the information regarding the display of the first pathological image.

Furthermore, the derivation device 100 performs learning with weighting based on information regarding a user corresponding to the viewing history information, or performs learning separately for each piece of the information regarding the user corresponding to the viewing history information. Furthermore, the information regarding the user corresponding to the viewing history information is information for specifying a diagnostician who has diagnosed the first pathological image or information indicating an ability rank of the diagnostician.

Thus, according to the above embodiments, the diagnosis support information can be derived with higher accuracy by using the information regarding the user corresponding to the viewing history information.

Furthermore, the derivation device 100 learns, in association with each other, the diagnostic information that indicates a positive diagnosis result and the viewing history information corresponding to the diagnostic information.

Thus, according to the above embodiments, the diagnosis support information is derived in consideration of the viewing history information in a positive case, and this improves the positive diagnosis accuracy.

Furthermore, the derivation device 100 learns, in association with each other, the diagnostic information that indicates a negative diagnosis result and the viewing history information corresponding to the diagnostic information.

Thus, according to the above embodiments, the diagnosis support information is derived in consideration of the viewing history information in a negative case, and this improves the negative diagnosis accuracy.

Furthermore, the derivation device 100 learns regions other than the attention region in the second pathological image as the diagnostic information that indicates a negative diagnosis result.

Thus, according to the above embodiments, a region to which attention is to be paid can be estimated with higher accuracy, and this further improves the diagnosis accuracy.

Furthermore, the derivation device 200 derives the diagnosis support information on the basis of viewing history information regarding a viewing history corresponding to the first pathological image having a similarity to the second pathological image higher than a threshold value, or the first pathological image having a degree of correlation with the second pathological image higher than a threshold value.

Thus, according to the above embodiments, the diagnosis accuracy can be improved on the basis of the diagnosis support information.

Furthermore, on the basis of the diagnosis support information, the display control device 23 controls an attention region, which is a region estimated to influence a diagnosis, to be visibly superimposed and displayed on the second pathological image. Furthermore, the display control device 23 performs a control to superimpose and display, on the second pathological image, a mask image that covers the attention region, a frame image that indicates an outer frame of the attention region, an arrow image pointing to the attention region, or text information describing the attention region.

Thus, according to the above embodiments, a region to be diagnosed with attention in the second pathological image is displayed, and this improves diagnosis accuracy and diagnosis efficiency.

Furthermore, the display control device 23 changes a display mode of the attention region in accordance with a degree of influence on the diagnosis or a degree of reliability of the diagnosis support information on the basis of the diagnosis support information. Furthermore, the display mode is saturation, luminance, or transmittance.

Thus, according to the above embodiments, the degree of influence or the degree of reliability is reflected in information displayed, and this improves diagnosis accuracy and diagnosis efficiency.

Furthermore, the display control device 23 performs a control to display a part of an image of the second affected tissue corresponding to the attention region.

Thus, according to the above embodiments, the region to which attention is to be paid itself is displayed, and this improves diagnosis accuracy and diagnosis efficiency.

Furthermore, in a case where there is a plurality of attention regions, the display control device 23 performs a control to display pathological images, each of which corresponds to one of the attention regions. Furthermore, the display control device 23 performs a control to display the pathological images, each of which corresponds to one of the attention regions, side by side in a display screen.

Thus, according to the above embodiments, it is possible to support diagnosis of the entire first affected tissue without omission.

Furthermore, the display control device 23 performs a control to display the pathological images, each of which corresponds to one of the attention regions, in the display screen in descending order of the degree of influence on the diagnosis or the degree of reliability of the diagnosis support information.

Thus, according to the above embodiments, the degree of influence or the degree of reliability is reflected in information displayed, and this improves diagnosis accuracy and diagnosis efficiency.

Furthermore, the display control device 23 performs a control to switch between and display the pathological images, each of which corresponds to one of the attention regions, in the same display area.

Thus, according to the above embodiments, it is possible to support diagnosis of the entire first affected tissue without omission.

Furthermore, the display control device 23 performs a control to switch between and display the pathological images, each of which corresponds to one of the attention regions, in the same display area in descending order of the degree of influence on the diagnosis or the degree of reliability of the diagnosis support information.

Thus, according to the above embodiments, the degree of influence or the degree of reliability is reflected in information displayed, and this improves diagnosis accuracy and diagnosis efficiency.

Furthermore, the diagnosis support information is a diagnosis result for the first affected tissue and a predicted diagnosis prediction result. Furthermore, the diagnosis prediction result is whether a lesion site has been found, a type of the lesion site, a degree of progression of the lesion site, or a probability of being the lesion site.

Thus, according to the above embodiments, additional information, which is the diagnosis prediction result, is derived, and this improves the diagnosis accuracy.

Note that the effects described herein are merely illustrative and are not intended to be restrictive, and other effects may be obtained.

Note that the present technology can also be configured as described below.

(1)

A diagnosis support program that causes an information processing device to execute:

an acquisition procedure of acquiring a first pathological image corresponding to a first affected tissue, history information regarding a history of viewing the first pathological image, and diagnostic information for the first affected tissue corresponding to the first pathological image; and a derivation procedure of deriving diagnosis support information for supporting diagnosis of a second pathological image corresponding to a second affected tissue to be diagnosed on the basis of the first pathological image, the history information, and the diagnostic information.

(2)

The diagnosis support program according to (1), in which the derivation procedure derives information regarding viewing as the diagnosis support information.

(3)

The diagnosis support program according to (1) or (2), in which the derivation procedure derives the diagnosis support information by using history information corresponding to the diagnostic information with a positive diagnosis result.

(4)

The diagnosis support program according to any one of (1) to (3), in which the history information includes information regarding an image of a partial region of the first pathological image saved at the time of diagnosis of the first pathological image.

(5)

The diagnosis support program according to (4), in which the derivation procedure acquires an image of a partial region of the first pathological image from a medical information system in which patient information corresponding to the first pathological image is registered.

(6)

The diagnosis support program according to any one of (1) to (5), in which the first pathological image is an entire image obtained by imaging the entire first affected tissue, and the history information is position information indicating a position where the first pathological image has been viewed.

(7)

The diagnosis support program according to (6), in which the history information is position information indicating a position where the first pathological image has been viewed, and information indicating a time or the number of times the first pathological image has been viewed.

(8)

The diagnosis support program according to any one of (1) to (7), in which the first pathological image is an image constituted by a partial image corresponding to each region of the first affected tissue, and the history information is partial image information indicating a viewed partial image among the partial images corresponding to the regions.

(9)

The diagnosis support program according to (8), in which the partial image information is information indicating a position of the partial image or specifying the partial image.

(10)

The diagnosis support program according to any one of (1) to (9), in which the derivation procedure derives the diagnosis support information on the basis of an attention region of the second pathological image estimated from the history information.

(11)

The diagnosis support program according to (10), in which the derivation procedure derives the diagnosis support information on the basis of the history information, assuming that a region with a larger display magnification is an attention region with a higher degree of attention, a region with a longer viewing time is an attention region with a higher degree of attention, or a region with a larger number of times of viewing is an attention region with a higher degree of attention.

(12)

The diagnosis support program according to any one of (1) to (11), in which the diagnostic information is information regarding whether a lesion site has been found, a type of the lesion site, or a degree of progression of the lesion site.

(13)

The diagnosis support program according to any one of (1) to (12), in which the diagnostic information is acquired from the medical information system in which patient information corresponding to the first pathological image is registered.

(14)

The diagnosis support program according to any one of (1) to (13), further causing the computer to execute a learning procedure of learning an association among the first pathological image, the history information, and the diagnostic information, in which the derivation procedure derives the diagnosis support information by using a result of learning by the learning procedure.

(15)

The diagnosis support program according to (14), in which the learning procedure performs learning with weighting based on information regarding the first affected tissue, or performs learning separately for each piece of the information regarding the first affected tissue.

(16)

The diagnosis support program according to (15), in which the information regarding the first affected tissue is information regarding a patient from which the first affected tissue has been collected, site information regarding the first affected tissue, a reagent used to stain the first affected tissue, or information regarding an organization that has stained the first affected tissue.

(17)

The diagnosis support program according to any one of (14) to (16), in which the learning procedure performs learning with weighting based on information regarding imaging of the first pathological image, or performs learning separately for each piece of the information regarding imaging of the first pathological image.

(18)

The diagnosis support program according to (17), in which the information regarding the imaging of the first pathological image is information regarding a device that has captured the first pathological image or an organization that has captured the first pathological image.

(19)

The diagnosis support program according to any one of (14) to (18), in which the learning procedure performs learning with weighting based on information regarding display of the first pathological image, or performs learning separately for each piece of the information regarding display of the first pathological image.

(20)

The diagnosis support program according to (19), in which the information regarding the display of the first pathological image is information regarding a device used to display the first pathological image, a program used to display the first pathological image, a viewing time of a region where the first pathological image is displayed, or the number of times the region where the first pathological image is displayed.

(21)

The diagnosis support program according to any one of (14) to (20), in which the learning procedure performs learning with weighting based on information regarding a user corresponding to the history information, or performs learning separately for each piece of the information regarding the user corresponding to the history information.

(22)

The diagnosis support program according to (21), in which the information regarding the user corresponding to the history information is information for specifying a diagnostician who has diagnosed the first pathological image or information indicating an ability rank of the diagnostician.

(23)

The diagnosis support program according to any one of (14) to (22), in which the learning procedure learns, in association with each other, the diagnostic information that indicates a positive diagnosis result and the history information corresponding to the diagnostic information.

(24)

The diagnosis support program according to any one of (14) to (23), in which the learning procedure learns, in association with each other, the diagnostic information that indicates a negative diagnosis result and the history information corresponding to the diagnostic information.

(25)

The diagnosis support program according to (24), in which the learning procedure learns regions other than the attention region in the second pathological image as the diagnostic information that indicates a negative diagnosis result.

(26)

The diagnosis support program according to any one of (1) to (25), in which the derivation procedure derives the diagnosis support information on the basis of history information regarding a viewing history corresponding to the first pathological image having a similarity to the second pathological image higher than a threshold value, or the first pathological image having a degree of correlation with the second pathological image higher than a threshold value.

(27)

A diagnosis support system including:

a microscope; and a derivation device that derives diagnosis support information, which is information for supporting diagnosis, in which the derivation device derives, on the basis of a first pathological image corresponding to a first affected tissue, history information regarding a history of viewing the first pathological image, and diagnostic information for the first affected tissue, diagnosis support information for supporting diagnosis of a second pathological image corresponding to a second affected tissue to be diagnosed that has been imaged by the microscope.

(28)

A diagnosis support system including: a microscope; and software used for processing of a pathological image corresponding to an object to be imaged by the microscope, in which the software causes an information processing device to execute, on the basis of a first pathological image corresponding to a first affected tissue, history information regarding a history of viewing the first pathological image, and diagnostic information for the first affected tissue, processing of deriving diagnosis support information for supporting diagnosis of a second pathological image corresponding to a second affected tissue to be diagnosed that has been imaged by the microscope.

(29)

The diagnosis support system according to (27) or (28), in which the diagnosis support system further includes a display control device, and the display control device controls, on the basis of the diagnosis support information, an attention region, which is a region estimated to influence a diagnosis, to be visibly superimposed and displayed on the second pathological image.

(30)

The diagnosis support system according to (29), in which the display control device performs a control to superimpose and display, on the second pathological image, a mask image that covers the attention region, a frame image that indicates an outer frame of the attention region, an arrow image pointing to the attention region, or text information describing the attention region.

(31)

The diagnosis support system according to (29) or (30), in which the display control device changes a display mode of the attention region in accordance with a degree of influence on the diagnosis or a degree of reliability of the diagnosis support information on the basis of the diagnosis support information.

(32)

The diagnosis support system according to (31), in which the display mode is saturation, luminance, or transmittance.

(33)

The diagnosis support system according to any one of (29) to (32), in which the display control device performs a control to display a part of an image of the second affected tissue corresponding to the attention region.

(34)

The diagnosis support system according to any one of (29) to (33), in which the display control device performs, in a case where there is a plurality of the attention regions, a control to display pathological images, each of which corresponds to one of the attention regions.

(35)

The diagnosis support system according to (34), in which the display control device performs a control to display the pathological images, each of which corresponds to one of the attention regions, side by side in a display screen.

(36)

The diagnosis support system according to (35), in which the display control device performs a control to display the pathological images, each of which corresponds to one of the attention regions, in the display screen in descending order of the degree of influence on the diagnosis or the degree of reliability of the diagnosis support information.

(37)

The diagnosis support system according to (34), in which the display control device performs a control to switch between and display the pathological images, each of which corresponds to one of the attention regions, in the same display area.

(38)

The diagnosis support system according to (37), in which the display control device performs a control to switch between and display the pathological images, each of which corresponds to one of the attention regions, in the same display area in descending order of the degree of influence on the diagnosis or the degree of reliability of the diagnosis support information.

(39)

The diagnosis support system according to any one of (28) to (38), in which the diagnosis support information is a diagnosis result for the first affected tissue and a predicted diagnosis prediction result.

(40)

The diagnosis support system according to (39), in which the diagnosis prediction result is whether a lesion site has been found, a type of the lesion site, a degree of progression of the lesion site, or a probability of being the lesion site.

(41)

A diagnosis support method including:

deriving, by a computer, on the basis of a first pathological image corresponding to a first affected tissue, history information regarding a history of viewing the first pathological image, and diagnostic information for the first affected tissue corresponding to the first pathological image, diagnosis support information for supporting diagnosis of a second pathological image corresponding to a second affected tissue to be diagnosed.

(42)

A diagnosis support system including: a medical image acquisition device; and software used for processing of a medical image corresponding to an object to be imaged by the medical image acquisition device, in which the software causes an information processing device to execute, on the basis of a first medical image corresponding to a first affected tissue, history information regarding a history of viewing the first medical image, and diagnostic information for the first affected tissue, processing of deriving diagnosis support information for supporting diagnosis of a second medical image corresponding to a second affected tissue to be diagnosed that has been imaged by the medical image acquisition device.

REFERENCE SIGNS LIST

1 Diagnosis support system
11, 21 Microscope
12, 22 Server
13, 23 Display control device
14, 24 Display device
23a Image acquisition unit
23b Display control unit
100, 200 Derivation device
131, 231 History information acquisition unit
132, 232 Diagnostic information acquisition unit
133 Learning unit
134, 234 Derivation unit

The invention claimed is:

1. A non-transitory computer readable medium storing a program which, when executed, causes a computer to perform processing comprising:
   a derivation procedure of deriving, on a basis of a first pathological image corresponding to a first affected tissue wherein the first pathological image comprises a plurality of pixels, history information regarding a history of viewing the first pathological image comprising a number of times the first pathological image was viewed and a length of time over which the first pathological image has been viewed and a position of a portion of the first pathological image that was enlarged and displayed, and diagnostic information for the first affected tissue corresponding to the first pathological image, diagnosis support information for supporting diagnosis of a second pathological image corresponding to a second affected tissue to be diagnosed; and
   a learning procedure comprising assigning at least one of the plurality of pixels an attention value based on a magnification ratio of the at least one pixel, a viewing time of the at least one pixel, a number of times the at least one pixel was viewed, generating a map image comprising the attention values corresponding to the plurality of pixels, and determining the diagnostic information for the first affected tissue corresponding to the first pathological image by identifying a first portion of the first pathological image having a positive result and a second portion of the first pathological image having a negative result.

2. The diagnosis support program according to claim 1, wherein
   the derivation procedure derives information regarding viewing as the diagnosis support information.

3. The diagnosis support program according to claim 1, wherein
   the first pathological image is an entire image obtained by imaging the entire first affected tissue, and
   the history information is position information indicating a position where the first pathological image has been viewed.

4. The diagnosis support program according to claim 3, wherein
   the history information is position information indicating a position where the first pathological image has been viewed, and information indicating a time or the number of times the first pathological image has been viewed.

5. The diagnosis support program according to claim 1, wherein
   the first pathological image is an image constituted by a partial image corresponding to each region of the first affected tissue, and
   the history information is partial image information indicating a viewed partial image among the partial images corresponding to the regions.

6. The diagnosis support program according to claim 1, wherein
   the derivation procedure derives the diagnosis support information on a basis of an attention region of the second pathological image estimated from the history information.

7. The diagnosis support program according to claim 6, wherein
   the derivation procedure derives the diagnosis support information on a basis of the history information, assuming that a region with a larger display magnification is an attention region with a higher degree of attention, a region with a longer viewing time is an attention region with a higher degree of attention, or a region with a larger number of times of viewing is an attention region with a higher degree of attention.

8. The diagnosis support program according to claim 1, wherein
   the diagnostic information is information regarding whether a lesion site has been found, a type of the lesion site, or a degree of progression of the lesion site.

9. The diagnosis support program according to claim 1, wherein the learning procedure learning an association among the first pathological image, the history information, and the diagnostic information, and
   wherein the derivation procedure derives the diagnosis support information by using a result of learning by the learning procedure.

10. The diagnosis support program according to claim 9, wherein
    the learning procedure learns, in association with each other, the diagnostic information that indicates a positive diagnosis result and the history information corresponding to the diagnostic information.

11. The diagnosis support program according to claim 9, wherein
    the learning procedure learns, in association with each other, the diagnostic information that indicates a negative diagnosis result and the history information corresponding to the diagnostic information.

12. The diagnosis support program according to claim 11, wherein
    the learning procedure learns regions other than an attention region in the second pathological image as the diagnostic information that indicates a negative diagnosis result.

13. The diagnosis support program according to claim 1, wherein
the derivation procedure derives the diagnosis support information on a basis of history information regarding a viewing history corresponding to the first pathological image having a similarity to the second pathological image higher than a threshold value, or the first pathological image having a degree of correlation with the second pathological image higher than a threshold value.

14. A diagnosis support system comprising:
a microscope; and
a derivation device that derives diagnosis support information, which is information for supporting diagnosis,
wherein the derivation device derives, on a basis of a first pathological image corresponding to a first affected tissue, history information regarding a history of viewing the first pathological image comprising a number of times the first pathological image was viewed and a length of time over which the first pathological image has been viewed and a position of a portion of the first pathological image that was enlarged and displayed, and diagnostic information for the first affected tissue, diagnosis support information for supporting diagnosis of a second pathological image corresponding to a second affected tissue to be diagnosed that has been imaged by the microscope; and a learning procedure,
wherein the learning procedures assigns at least one of the plurality of pixels an attention value based on a magnification ratio of the at least one pixel, a viewing time of the at least one pixel, a number of times the at least one pixel was viewed, generates a map image comprising the attention values corresponding to the plurality of pixels, and determines the diagnostic information for the first affected tissue corresponding to the first pathological image by identifying a first portion of the first pathological image having a positive result and a second portion of the first pathological image having a negative result.

15. The diagnosis support system according to claim 14, wherein
the diagnosis support system further includes a display control device, and
the display control device controls, on a basis of the diagnosis support information, an attention region, which is a region estimated to influence a diagnosis, to be visibly superimposed and displayed on the second pathological image.

16. The diagnosis support system according to claim 15, wherein
the display control device changes a display mode of the attention region in accordance with a degree of influence on the diagnosis or a degree of reliability of the diagnosis support information on a basis of the diagnosis support information.

17. The diagnosis support system according to claim 15, wherein
the display control device performs a control to display a part of an image of the second affected tissue corresponding to the attention region.

18. The diagnosis support system according to claim 14, wherein
the diagnosis support information is a diagnosis result for the first affected tissue and a predicted diagnosis prediction result.

19. The diagnosis support system according to claim 18, wherein
the diagnosis prediction result is whether a lesion site has been found, a type of the lesion site, a degree of progression of the lesion site, or a probability of being the lesion site.

20. A diagnosis support method comprising:
deriving, by a computer, on a basis of a first pathological image corresponding to a first affected tissue, history information regarding a history of viewing the first pathological image comprising a number of times the first pathological image was viewed and a length of time over which the first pathological image has been viewed and a position of a portion of the first pathological image that was enlarged and displayed, and diagnostic information for the first affected tissue corresponding to the first pathological image, diagnosis support information for supporting diagnosis of a second pathological image corresponding to a second affected tissue to be diagnosed;
assigning, by the computer, at least one of the plurality of pixels an attention value based on a magnification ratio of the at least one pixel, a viewing time of the at least one pixel, a number of times the at least one pixel was viewed,
generating, by the computer, a map image comprising the attention values corresponding to the plurality of pixels, and
determining, by the computer, the diagnostic information for the first affected tissue corresponding to the first pathological image by identifying a first portion of the first pathological image having a positive result and a second portion of the first pathological image having a negative result.

21. A diagnosis support system comprising:
a microscope; and software used for processing of a pathological image corresponding to an object to be imaged by the microscope,
wherein the software causes an information processing device to execute, on a basis of a first pathological image corresponding to a first affected tissue, history information regarding a history of viewing the first pathological image comprising a number of times the first pathological image was viewed and a length of time over which the first pathological image has been viewed and a position of a portion of the first pathological image that was enlarged and displayed, and diagnostic information for the first affected tissue, processing of deriving diagnosis support information for supporting diagnosis of a second pathological image corresponding to a second affected tissue to be diagnosed that has been imaged by the microscope; and
wherein the software further causes the information processing device to execute a learning procedure comprising assigning at least one of the plurality of pixels an attention value based on a magnification ratio of the at least one pixel, a viewing time of the at least one pixel, a number of times the at least one pixel was viewed, generating a map image comprising the attention values corresponding to the plurality of pixels, determining the diagnostic information for the first affected tissue corresponding to the first pathological image by identifying a first portion of the first pathological image having a positive result and a second portion of the first pathological image having a negative result.

* * * * *